United States Patent [19]

Niman et al.

[11] Patent Number: 5,030,565
[45] Date of Patent: Jul. 9, 1991

[54] POLYPEPTIDE-INDUCED MONOCLONAL RECEPTORS TO PROTEIN LIGANDS

[75] Inventors: Henry L. Niman, Carlsbad; Richard A. Lerner, La Jolla, both of Calif.

[73] Assignee: Scripps Clinic and Research Foundation, La Jolla, Calif.

[21] Appl. No.: 701,954

[22] Filed: Feb. 15, 1985

Related U.S. Application Data

[63] Continuation-in-part of PCT US84/01304, Aug. 17, 1984, which is a continuation-in-part of Ser. No. 524,084, Aug. 17, 1983, abandoned.

[51] Int. Cl.$^5$ ............................................. G01N 33/577
[52] U.S. Cl. ..................................... 435/70.21; 422/61; 435/172.2; 435/240.22; 436/548; 436/813; 530/324; 530/325; 530/326; 530/327; 530/328; 530/329; 530/387; 530/413
[58] Field of Search ...................... 435/68, 172.2, 240, 435/70.21, 240.27; 436/548, 813; 530/387, 324-329, 413; 422/61

[56] References Cited

U.S. PATENT DOCUMENTS 4,532,220  7/1985  Lavi ................................. 436/813 X
4,535,058  8/1985  Weinberg ......................... 436/813 X
4,699,877  10/1987 Cline ..................................... 435/6

FOREIGN PATENT DOCUMENTS 8403087  8/1984  World Int. Prop. O. ............ 103/52

OTHER PUBLICATIONS

Gentry et al., J. Biol. Chem., 258:11219-11228 (1983).
Tamura et al., Cell 34:587-596 (1983).
Arneheiter et al., Nature 294:278-380 (1981).
Gonda, T. J. et al., Molecular and Cellular Biology, 2(6), 617-624 (Jun. 1982).
Der, C. J. et al., Proc. Natl. Acad. Sci., U.S.A., 79(11), 3637-3640 (Jun. 1982).
Furth, M. E. et al., J. Virol., 43(1), 294-304 (Jul. 1982).
Chemical Abstracts, 98:103976a (Mar. 1983).
Chemical Abstracts, 99:137927w (Oct. 1983).
Young and Atassi, Immunological Communications 11(1):9-16 (Jul. 23, 1982).
Schmitz, Atassi and Atassi, Molecular Immunology 19:1699-1702 (Dec. 1982).
Sutcliffe et al., Science 219:660-666 (Feb. 11, 1983).
Bulinski, International Review of Cytology 103:281-303 (1986).
Niman et al., PNAS-U.S.A. 80:4949-4953 (1983).
Newmark News and Views, Nature 305:9 (Sept. 1983).
Baltimore, TBIS 9:137-138 (Apr. 1984).
Sutcliffe et al., Nature 287:801-805 (Oct. 1980).
Sen et al., PNAS-USA 80:1246-1250 (Mar. 1980).
Wong and Goldberg PNAS-USA 78:7412-7416 (Dec. 1981).
Papkoff et al., Cell 27:109-119 (Nov. 1981).
Papkoff et al., Cell 29:417-426 (Jun. 1982).
Tamura and Bauer, EMBO J. 1:1479-1485 (1982).

Primary Examiner—Christine Nucker
Attorney, Agent, or Firm—Lyon & Lyon

[57] ABSTRACT

Monoclonal receptors raised to immunogenic polypeptides whose amino acid residue sequences correspond to sequences of oncoprotein ligands are disclosed, as are method for the production of those receptors and products and methods that utilize them. The monoclonal receptors bind both to the oncoprotein ligand to a portion of which the polypeptide corresponds in sequence, and to the immunogenic polypeptide to which the receptors were raised.

31 Claims, 16 Drawing Sheets

CONSERVED KINASE REGION 1

| Oncogene | Residue Positions | Polypeptide Sequence |
|---|---|---|
| fes$^{ST}$ | 519-530 | IGRGNFGEVFSG |
| fes$^{GA}$ | 702-713 | IGRGNFGEVFSG |
| fps | 927-938 | IGRGNFGEVFSG |
| src | 273-284 | LGQGCFGEVWMG |
| yes | 557-568 | LGQGCFGEVWMG |
| fgr | 310-321 | LGQGCFGEVWLG |
| fms | 618-629 | LGTGAFGKVYEA |
| erb B | 138-149 | LGTGAFGTIYKG |
| mht | 91-102 | IGSGSFGTVYKG |
| raf | 30-41 | IGSGSFGTVYKG |
| abl | 368-379 | LGGGQYGEVYEG |
| mos | 100-111 | LGSGGFGSVYKA |

FIG. 15.

CONSERVED KINASE REGION 2

| Oncogene | Residue Positions | Polypeptide Sequence |
|---|---|---|
| fes$^{ST}$ | 674-688 | VPVKWTAPEALNYGR |
| fes$^{GA}$ | 857-871 | VPVKWTAPEALNYGR |
| fps | 1082-1096 | IPVKWTAPEALNYGW |
| src | 424-438 | FPIKWTAPEAALYGR |
| yes | 708-722 | FPIKWTAPEAALYGR |
| fgr | 461-475 | FPIKWTAPEAALYGR |
| fms | 847-862 | LPVKWMAPESIFOCV |
| erb B | 296-310 | VPIKWMALESILHRI |
| mht | 238-253 | GSVLWMAPEVIRMQD |
| raf | 177-192 | GSVLWMAPEVIRMQD |
| abl | 521-535 | FPIKWRAPESLAYNK |
| mos | 269-284 | GTYTHQAPEILKGEI |

FIG. 16.

CONSERVED KINASE REGION 3

| Oncogene | Residue Positions | Polypeptide Sequence |
|---|---|---|
| fes$^{ST}$ | 744-759 | LMEQCWAYEPGQRPSF |
| fes$^{GA}$ | 927-942 | LMEQCWAYEPGQRPSF |
| fps | 1152-1167 | LMQRCWEYDPHRRPSF |
| src | 494-509 | LMCQCWRKDPEERPTF |
| yes | 770-793 | LMKLCWKKDPDERPTF |
| fgr | 531-546 | AMEQTWRLDPEERPTF |
| fms | 910-933 | FMQACWALEPTRRPTF |
| erb B | 366-381 | IMVKCWMIDADSRPKF |
| mht | 316-331 | LVADCLKKVREERPLE |
| raf | 255-270 | LVADCVKKVKEERPTF |
| abl | 591-606 | LMRACWQWNPSDRPSF |
| mos | 344-359 | IIQSCWEARGLQRPTF |
| rel | 382-397 | TLHSCWQQLYSPSPSA |

POLYPEPTIDE-INDUCED MONOCLONAL RECEPTORS TO PROTEIN LIGANDS

CROSS REFERENCE TO RELATED APPLICATION

This is a continuation-in-part application of copending PCT application PCT/US84/01304 filed Aug. 17, 1984 wherein the U.S. National Phase was entered on Feb. 15, 1985, that is a continuation-in-part application of copending U.S. application Ser. No. 524,084, filed Aug. 17, 1983 now abandoned.

TECHNICAL FIELD

The present invention relates to immunological receptors and ligands, and more particularly to monoclonal receptors raised to polypeptides whose amino acid residue sequences correspond to sequences of retroviral oncoprotein ligands.

BACKGROUND ART

Retroviruses are viruses that contain a single strand of RNA as the genetic material rather than DNA. The single-stranded RNA genome of each of these viruses gives rise to a double-stranded DNA molecule after the virus infects a susceptible host. This DNA replica of the viral genome then introduces itself permanently into a chromosome of the successfully infected cell and replicates in that host chromosome.

The retroviruses discussed hereinafter and in the claims may be further defined as being replication-defective retroviruses. Thus, these viruses do not themselves contain a gene encoding the reverse transcriptase usually required to permit the viral RNA genome to be translated into a DNA that can be introduced into a chromosome fo the infected host. Rather, the retroviruses discussed hereinafter typically must be complimented in their infection by a so-called helper virus that is replication-competent. That second virus contains the gene that encodes the reverse transcriptase enzyme that incorporates the genomic materials from both viruses into the successfully infected host cells to transform those cells.

For ease in understanding, the replication-defective retroviruses will be discussed hereinafter and in the claims merely as retroviruses with the understanding that they are replication-defective and require the assistance of a helper virus for successful infection and transformation of host cells. This usage of the term retrovirus is known in the art and has been used in the art as such without further explanation.

Some members of the retrovirus family are highly oncogenic as judged by their ability to cause the formation of solid tumors within a short period of time after being inoculated into the host. These viruses can also cause "cancerous" changes in cells grown and cultured in the laboratory; such changes are called "transformations" and provide a reliable in vitro biological assay for oncogenic viruses. Several such viruses have been isolated from chickens, turkeys, mice, rats, cats and monkeys.

A single gene, the oncogene, located on the genome of these highly oncogenic viruses is responsible for the tumorgenic potential of the virus. In the case of several viruses, the protein products of their oncogenes, referred to herein as oncoproteins, have been immunologically identified by taking advantage of the fact that serum from an animal bearing a virus-induced tumor contains antibodies directed against those oncoproteins.

A rapidly growing body of evidence indicates that the oncogenes of retroviruses are closely related to and are derived from specific genetic loci in the normal cellular genetic information of all vertebrates. Molecular hybridization studies using specific nucleic acid probes done during the middle 1970's, followed by genetic cloning of viral oncogenes and their cellular relatives by recombindant DNA technology, have established the kinship between retroviral oncogenes (v-onc) and cellular oncogenes (c-onc) found in all normal vertebrate cells.

Molecular analysis of the nearly two dozen retroviruses thus far isolated has revealed more than a dozen different oncogenes, each distinguished by its nucleotide sequence, and each with a corresponding cellular oncogenic homolog. For example, the human EJ or T24 bladder carcinoma oncogene was identified as the homolog of the transforming gene of Harvey murine sarcoma virus ($ras^{Ha}$) and also of the BALB sarcoma virus (bas) [Parada et al., Nature, 297, 474–478 (1982); Der et al., Proc. Natl. Acad. Sci. USA, 79, 3627–3634 (1982); and Santos et al., Nature, 298, 343–347 (1982)]. In addition, the oncogene of the human carcinoma cell line LX-1 was found to be homologous to the transforming gene of Kirsten strain of murine sarcoma virus ($ras^{Ki}$) [Der et al., above]. Still further, the same v-onc for a c-onc designated fps of avian origin is represented at least twice among a limited number of avian retrovirus isolates; its mammalian cognate designated fes in feline species is found in two different strains of feline sarcoma viruses. Moreover, recent work has found a sequence homology between human platelet-derived growth factor (PDGF) and the oncoprotein encoded by the simian sarcoma oncogene, v-sis, and denominated $p28_{sis}$ [Antoniades et al., Science, 220, 963–965 (1983) and Devare et al., Proc. Natl. Acad. Sci. USA, 80, 731–735 (1983)].

The structural and immunological relatedness between the transforming sis gene product ($p28^{sis}$) of simian sarcoma virus and platelet derived growth factor (PDGF) provides the most solid link between the transforming properties of oncogenes and the mitogenic action of growth factors. The sis gene is one of many oncogenes that have been transduced by retroviruses. These captured genes have been highly conserved through evolution, suggesting they serve important physiological functions. PDGF is a very potent mitogen for many connective tissue cell types in culture. It is stored in the alpha granules of platelets, and is released at sites of vascular damage. PDGF binding to specific cell surface receptors triggering a tyrosine-specific protein kinase activity. This event identifies a common mechanism used by a wide variety of growth factors and oncogenes.

Insulin, gastrin, epidermal growth factor (EGF) and transforming growth factors all bind to receptors that are associated with tryosine protein kinase activity. The oncogenes src, yes, fes, fps, ros, abl, fgr have tyrosine kinase activity while the oncogenes mos, raf, mht, and erb-B have sequence homology to kinase domain. Furthermore, sequence analysis of fragments of the EGF receptor demonstrate a very close homology with the predicted sequence of erb-B. Thus, the binding of a growth factor to a receptor with tyrosine kinase activity appears to be a common event in mitogenesis and transformation.

The precise molecular mechanisms of this interaction are not known. PDGF isolated from platelets contains two polypeptide chains that form disulfide bonded complexes that migrate on denaturing polyacrylamide gels between 20,000 to 35,000 daltons. Reduction destroys the biological activity of these complexes and produces proteins that migrate between 14,000 and 18,000 daltons. Sequence analysis of the material migrating at 18,000 daltons identifies two homologous but distinct sequences.

As discussed before, one of these sequences (PDGF-2) is highly homologus to the protein ($p28^{sis}$) predicted by the nucleotide sequence of the simian sarcoma virus oncogene (sis). The homology begins at residue 67 and extends at least to residue 171. Recently, the isolation and sequencing of a human c-sis clone has extended this homology to the predicted carboxy-terminus. The open reading frame encoding the sequenced PDGF-2 region continues upstream, indicating PDGF isolated fom platelets is derived from a larger precursor, consistent with the 4.2 kb sis-related mRNA detected in various cell lines.

The protein encoded by the viral oncogene and having a corresponding, homologous protein within the host cell are both referred to herein as oncoproteins, although the cellular oncoprotein is typically present in small quantities in normal cells, and thus need not only be associated with neoplastic states. In addition, oncoproteins encoded by related oncogenes may have different molecular weights, e.g., the p85 and p108 oncoproteins encoded by $v\text{-fes}^{ST}$ and $v\text{-fes}^{GA}$, respectively, and the 100-105k dalton protein of normal mink cells thought to be encoded by the c-fes gene. [Sen et al., Proc. Natl. Acad. Sci. USA, 80, 1246-1250 (1983).]The term oncoprotein is thus used generally herein for proteins whose genes and amino acid residue sequences are homologous, at least in part.

The oncoprotein is generally not present in the virus particle that infects the cell, but is only expressed after infection and transformation. The corresponding cellular oncoprotein is expressed at most minimally in normal cells and to a greater extent in neoplastic cells. Thus, the oncoprotein cannot typically be obtained from the virus. In addition, isolation of oncoproteins from cells is made difficult because of the small amount present, the complex mixture of proteins found in normal cells, and the relatively small amount of such proteins present even in transformed cells.

Oncoproteins encoded by v-onc and c-onc genes thus typically contain large sequences of amino acid residues that are homologous, but nevertheless are not usually identical. In addition, oncoproteins encoded by genes of different viral strains, each of which contains ostensibly the same oncogene, have been found to have slight variations in their amino acid residue sequences as exemplified above, and by the four published sequences of the ras gene which differ at the position of the twelfth amino acid residue. Thus, even when oncoproteins are in hand, it may be difficult to distinguish among them.

Immunologically induced receptor molecules such as monoclonal and polyclonal antibodies or the idiotype-containing portions of those antibodies are useful in purifying protein ligands to which they bind, as diagnostic reagents for assaying the presence and quantity of the protein ligands, as well as for distinguishing among homologous protein ligands.

The difficulties associated with obtaining quantities of oncoproteins typically militate against the preparation of receptors to those oncoproteins, although whole cell-induced monoclonal antibodies to v-fes and v-fps encoded oncoprotein have been reported by Veronese et al., J. Virol., 43, 896-904 (1982). In addition, even were whole proteins available for use as immunogens for inducing the production of such receptors, the use of large protein molecules as immunogens produces antisera containing polyclonal antibodies to the numerous epitopes of the large protein molecules.

Hybridoma and monoclonal antibody techniques utilizing whole proteins or large protein fragments as immunogens have been useful in narrowing the immunological response to such immunogens. However, such technology as heretofore practiced has been extremely time consuming and has provided only a relatively small number of hybridomas that secrete useful antibodies that recognize the immunogen. Moreover, even when successful, such techniques cannot be predictive of the chemical identity of epitope to which the receptor molecules are raised. Consequently, even after immunogen-recognizing receptors are produced, the obtaining of receptors to specific, chemically identified epitopic portions of the protein ligand has been a hit or miss operation that still further reduces the number of useful hybridomas that are ultimately produced.

Arnheiter et al., Nature, 294, 278-280 (1981) reported on the production of monoclonal antibodies that were raised to a polypeptide that contained 56 amino acid residues and corresponded in amino acid residue sequence to the carboxy-terminal portion of an intact interferon molecule. That 56-mer polypeptide thus corresponded to approximately one-third of the sequence of the intact molecule.

Arnheiter et al. reported on the production of eleven monoclonal antibodies. However, only one of those eleven monoclonal antibodies bound both to the polypeptide immunogen and also to the intact interferon molecule. In addition, that binding was not very strong as judged by the 3000-fold excess of intact interferon required to compete the antibody away from the synthetic polypeptide. None of the other monoclonal antibodies bound to the intact molecule.

In addition, the production of the hybridomas secreting those monoclonal antibodies required the spleens from three immunized mice. The low yield of the desired interferon-binding monoclonal antibodies, and the fact that three mouse spleens were needed for the preparation of those hybridoma cell lines indicates that those workers were relatively unsuccessful in their efforts.

Lerner et al. have been successful in obtaining protection of animals by the use of vaccines against pathogens by utilizing synthetic amino acid residue sequences of short to moderate length as immunogens. See Sutcliffe et al., *Science*, 219, 495-497 (1983).

However, it must be understood that until the present invention, successful preparation of hybridomas and their secreted monoclonal receptors differs from the successful preparation of a vaccine containing oligoclonal receptors. Thus, for a high yield monoclonal antibody preparation, it is necessary to stimulate B-cells to secrete large amounts of avid antibodies. On the other hand, for a synthetic vaccine, a wider spectrum of oligoclonal antibodies may be produced in smaller amounts and with lower avidities. In addition, protection of an animal against a pathogen typically requires both T-cell and B-cell activations so that a cellular response and a humoral response, respectively, can be induced in the animal.

A popular explanation for the success of synthetic polypeptide-containing vaccines in generating antibodies that recognize intact proteins and protect animal hosts involves a stochastic model in which the diversity of the immune response allows the observation of an infrequent event; i.e., the polypeptide adopting the conformation of its corresponding sequence in the native molecule. The concept that moderate-length polypeptides can frequently conform to native structures is contrary to theoretical and experimental studies. Rather, such polypeptides are thought to exist as an ensemble of a large number of transient conformational states that are in dynamic equilibrium. T-Cell activation by, and B-cell production of antibodies raised to, some of that conformational ensemble have been believed sufficient to provide protection upon vaccination.

BRIEF SUMMARY OF THE INVENTION

The present invention contemplates monoclonal receptor molecule that binds both (a) to a protein ligand encoded by a retrovirus gene, and (b) to a polypeptide of moderate length, about 7 to about 40 residues, and preferably about 10 to about 30 amino acid residues, having an amino acid residue sequence corresponding to an amino acid residue sequence of a portion of the protein encoded by a gene of a retrovirus. The receptor molecule is raised to (induced by) an immunogen containing the polypeptide. Most preferably, the receptor molecule is a monoclonal receptor such as IgG or IgM class of immunoglobulins.

Specific, preferred monoclonal receptor molecules of this invention bind to proteins encoded by the genes listed below, and also to the polypeptide(s) listed opposite those genes:

| Gene | Polypeptide |
|---|---|
| fes | SDVWSFGILLWETFSLGASPYPNLSNQQTR; SPYPNLSNQQTR; IHRDLAARNCLVTEKN; IGRGNFGEVFSG; LMEQCWAYEPGQRPSF; VPVKWTAPEALNYGR; and SSGSDVWSFGILLWE |
| myb | RRKVEQEGYPQESSKAG; and RHYDEDPEKEKRIKELEL; |
| sis | RKIEIVRKKPIFKKATV; and RVTIRTVRVRRPPKGKHRKC; |
| ras | YREQIKRVKDSDDVPMVLVGNKC; and KLVVVGAR(S,V,G)GVGK; wherein the amino acid residues in parentheses are each an alternative to the immediately preceding amino acid residue in the formula; |
| myc | CDEENFYQQQQQSEL; PAPSEDIWKKFEL; LPTPPLSPSRRSGLC; CDPDDETFIKNIIQDC; CSTSSLYLQDLSAAASEC; CASQDSSAFSPSSDSLLSSTESSP; and CTSPRSSDTEENVKRRT; and |
| mos | LPRELSPSVDSR; RQASPPHIGGTY; and TTREVPYSGEPQ; |
| erb-B | ENDTLVRKYADANAVCQ LGSGAFGTIYKG IMVKCWMIDADSRPKF |
| PDGF-2 | SLGSLTIAEPAMIAECKT; RKIEIVRKKPIFKKATV; and RVTIRTVRVRRPPKGKHRKC; and |
| PDGF-1 | SIEEAVPAVCKT. |

The present invention also contemplates a method of producing monoclonal receptor molecules to a protein molecule ligand. In this method, an immunogenic polypeptide of moderate length (about 7 to about 40 residues), preferably synthetically produced, or a conjugate of that polypeptide bound to a carrier is provided. The amino acid residue sequence of that polypeptide corresponds to a portion of the amino acid residue sequence of a protein ligand. That immunogenic polypeptide, when bound as a conjugate to a carrier to keyhold limpet hemocyanin and used to immunize a mouse, is sufficiently immunogenic and antigenic to provide a 50 percent binding titer of the immunized mouse's serum to the polypeptide of at least about a 1:400 dilution after three immunications, each containing at least 10 micrograms of polypeptide in the conjugate and using complete Freund's adjuvant for the first immunication and alum as adjuvant in the second and third immunizations.

A mammal is hyperimmunized with the immunogenic polypeptide or a conjugate of that polypeptide bound to a carrier to provide a hyperimmune serum that exhibits a 50 percent binding titer to the polypeptide of at least about a 1:400 dilution. The receptor molecules of that serum also bind to the protein molecule ligand to which the polypeptide corresponds in amino acid residue sequence.

The hyperimmunized mammal is maintained for a period of at least about 30 days after the administration of the immunization that produces a 50 percent binding titer of a dilution of at least about 1:400. A booster immunization, as by intravenous injection, is thereafter administered to the animal.

Antibody-producing cells such as spleen cells (splenocytes) of the boosted mammal are fused with myeloma cells within a period of about three to about five days from the day of booster administration to prepare hybridoma cells. The hybridoma cells so prepared are assayed for the production of monoclonal receptor molecules that bind to a protein molecule ligand to a portion of which the immunogenic polypeptide corresponds in amino acid residue sequence. Preferably, the hybridoma cells are also assayed for the production of monoclonal receptor molecules that bind to the polypeptide.

The hybridoma cells that produce monoclonal receptor molecules that bind to the protein molecule ligand are then cultured to prepare an additional quantity of such cells. In preferred practice, those hybridoma cells that are cultured are also those that produce monoclonal receptors that bind to the polypeptide.

Another embodiment of the present invention contemplates a diagnostic system such as a kit for assaying for the presence of an oncoprotein ligand. This system includes at least a first package containing monoclonal receptor molecules of this invention. Admixing a predetermined amount of those receptors with a predetermined amount of an aqueous composition to be assayed for the presence of an oncoprotein ligand forms a receptor-ligand complex by an immunological reaction when the oncoprotein ligand includes an amino acid residue sequence corresponding to the amino acid residue sequence of the polypeptide bound by the receptor molecule. The presence of the complex can be identified by a label that is preferably contained in a second package of the system. Preferred oncoprotein ligand-containing aqueous composition is amniotic fluid or concentrated urine. The urine concentrate is easily obtained by noninvasive means and is readily concentrated to allow the implementation of the diagnostic test set forth herein.

Cell extracts and media conditioned by transformed cells are also suitable aqueous compositions containing oncoprotein ligands.

An ELISA assay is another contemplated embodiment of this invention. Here, an aqueous composition to be assayed for the presence of an oncoprotein ligand, such as concentrated urine is bound or otherwise affixed to a solid matrix such as a microtiter test well to form a solid support. A liquid solution containing a monoclonal receptor of this invention is admixed with the solid support to form a solid-liquid phase admixture. The solid-liquid phase admixture is maintained for a time period sufficient for the monoclonal receptor to bind to (immunoreact with) oncoprotein ligand of the solid support, i.e., affixed to the solid matrix. The solid and liquid phases are thereafter separated, and the amount of monoclonal receptor bound to the solid support and thereby the amount of oncoprotein ligand in the assayed sample are determined. Such determinations are typically carried out using a radioisotope- or enzyme-labeled antibody or Staphylococcus aureus protein A that binds specifically to a monoclonal receptor of this invention.

In yet another embodiment of this invention, monoclonal receptor molecules form the active, binding portions of an affinity-sorbant useful for binding and purifying oncoprotein ligands. Here, the receptors are linked to a solid support that is chemically inert to the oncoprotein such as agarose or cross-linked agarose. The affinity sorbant so prepared may then be admixed with an aqueous composition containing a protein ligand to form a reversible receptor-ligand complex when the protein ligand has an amino acid residue sequences corresponding to the amino acid residue sequence of the polypeptide bound by the receptor. The complex so formed can be thereafter dissociated to provide the protein ligand in a purified form.

The present invention provides several benefits and advantages.

One benefit of the invention is monoclonal receptor molecules that bind to epitopes contained in polypeptides of known amino acid residue sequence.

Another benefit of the invention is that monoclonal receptor molecules can be raised that bind to epitopes contained in known amino acid residue sequences of protein ligands encoded by retroviruses where those protein ligands are not needed to induce the production of the receptor molecules.

One of the advantages of the present invention is the high yield method of producing monoclonal receptors that bind to both an immunogenic polypeptide of moderate length and to a protein ligand molecule to whose amino acid residue sequence the polypeptide corresponds in part.

Another advantage of this invention is the provision of a diagnostic system such as a kit containing monoclonal receptor molecules capable of assaying for the presence of an oncoprotein.

A further advantage of this invention is the provision of a diagnostic method that can be accomplished using body samples obtained by non-invasive means.

Another advantage of this invention is that proteins of differing molecular weights may be detected allowing a differential and highly accurate assessment of the precise oncogenes being expressed within the organism.

Still further benefits and advantages of the present invention will be apparent to those skilled in the art from the description and claims that follow.

BRIEF DESCRIPTION OF THE DRAWINGS

In the drawings forming a part of this disclosure:

FIG. 2 is a photograph of an autoradiograph illustrating an immunological assay for detecting the presence of the FeSV fusion protein denominated p85 (85 kilodaltons; 85K daltons) by Western blot procedures similar to those of FIG. 1. Cell extracts of approximately $2 \times 10^6$ MSTF cells were electrophoresed into a 5–17 percent polyacrylamide gel, and then electrophoretically transferred to nitrocellulose strips. The strips of nitrocellulose were incubated with 5 milliliters each of hybridoma culture supernatant diluted 1:50 from hybridomas denominated S10F03 (lane A); P43D09 (lane B); P42C10 (lane C); P44El1 (lane D); or with R206B08, an anti-Rauscher gp70 protein receptor-producing hybridoma [Niman and Elder, Proc. Natl. Acad. Sci. USA, 77, 4524–4528 (1980)], as a negative control (lane E).

Figure 2:
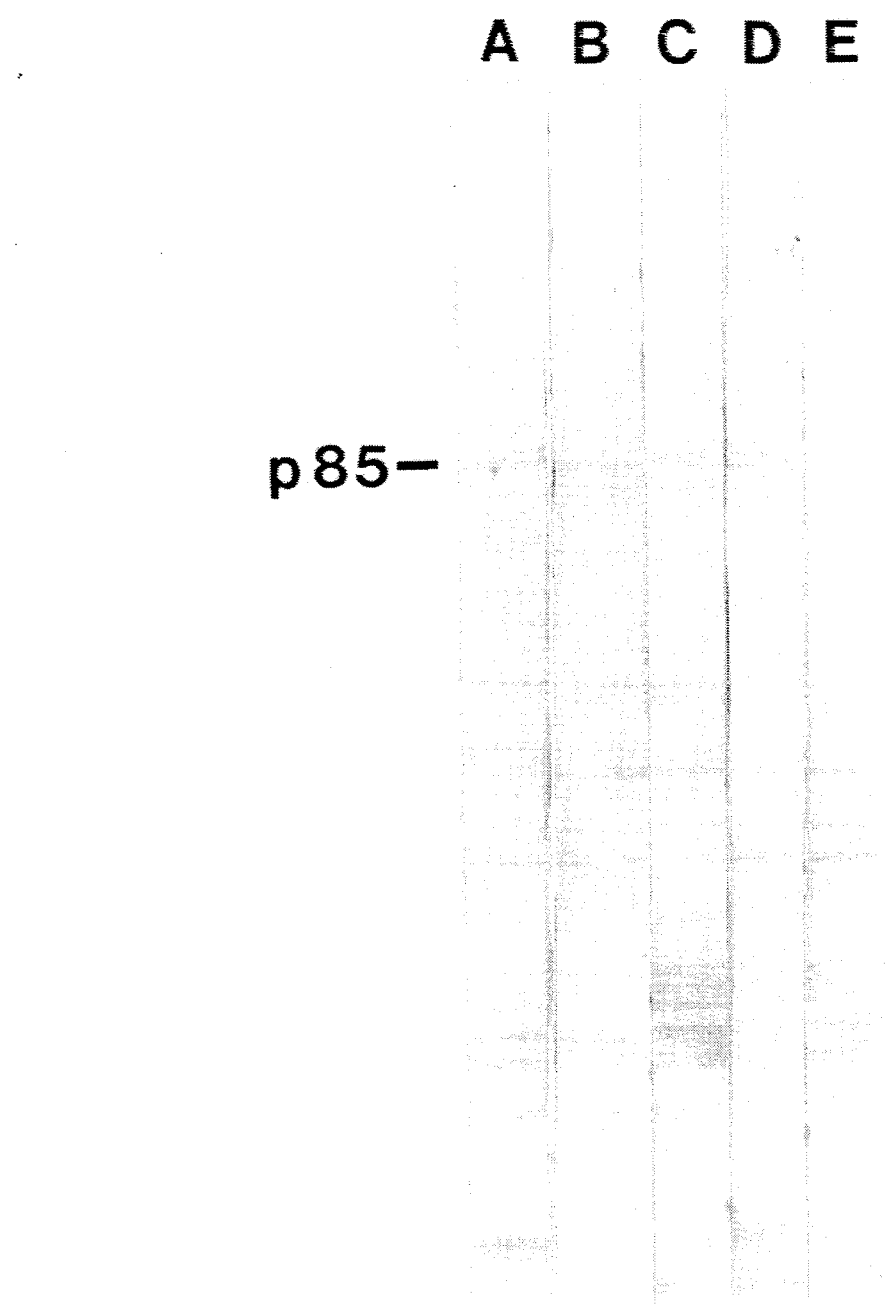

Binding was visualized by addition of peroxidase-labeled rabbit anti-mouse IgG as is discussed in the Materials and Methods section, hereinafter. The marker "p85-" at the left side of FIG. 2 illustrates the migration position of the 85k dalton ST-FeSV polyprotein encoded by the fes gene.

As can be seen from the proteins in lane E, this technique permits visualization of protein molecules that are not specifically bound by the monoclonal receptors of this invention. Subtraction of the non-specifically bound proteins visualized in lane E from the proteins visualized in lanes A-D illustrates that the only specifically bound protein is the p85 oncoprotein encoded by v-fes.

Figure 3:
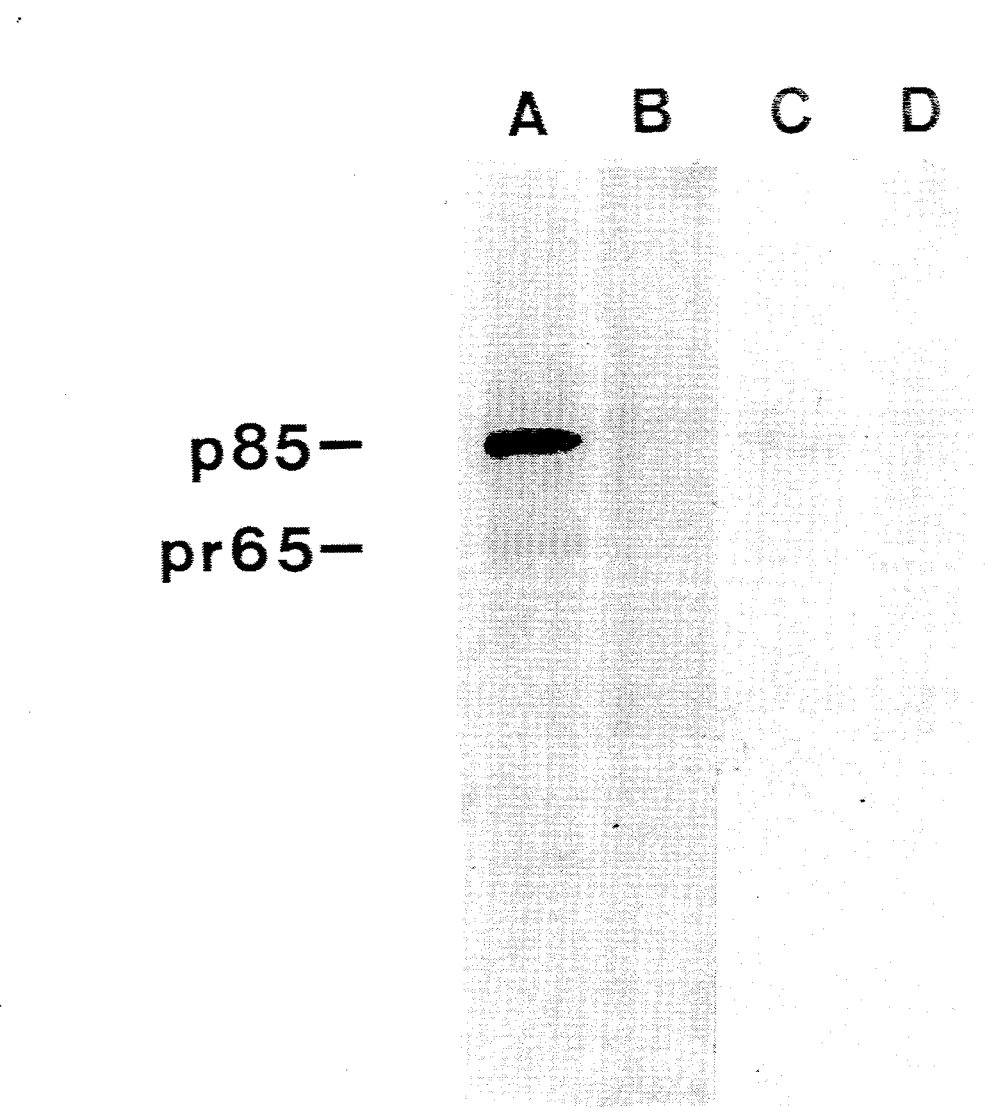

FIG. 3 is a photograph of an autoradiograph illustrating an immunoprecipation assay for the presence of the $^{32}$P-labeled FeSV fusion protein denominated p85. CCL64 mink cells (MSTF cells; lanes B and D) or those infected with FeLV-B and FeSV (MSTF cells; lanes A and C) were each labeled for 2 hours with 1 microcurie of $^{32}$P. The labeled cell extracts were then incubated with 5 microliters of goat anti-FeLV p15 antibodies (lanes A and B) or with 50 microliters of supernatant from cultured hybridoma S10F03 (lanes C and D). Immune complexes so prepared were collected using Staphylococcus aureus bacteria expressing protein A. The precipitated complexes so collected were washed, and were then dissociated into their component parts. The proteins were thereafter analyzed under reducing denaturing electrophoresis using a 5–17 percent polyacrylamide gel. The markers "p85-" and "pr65-" at the left of FIG. 3 illustrate migration positions of the 85K dalton ST-FeSV fusion protein encoded by the fes gene, and the 65K dalton FeLV gag-precursor protein.

Figure 4:
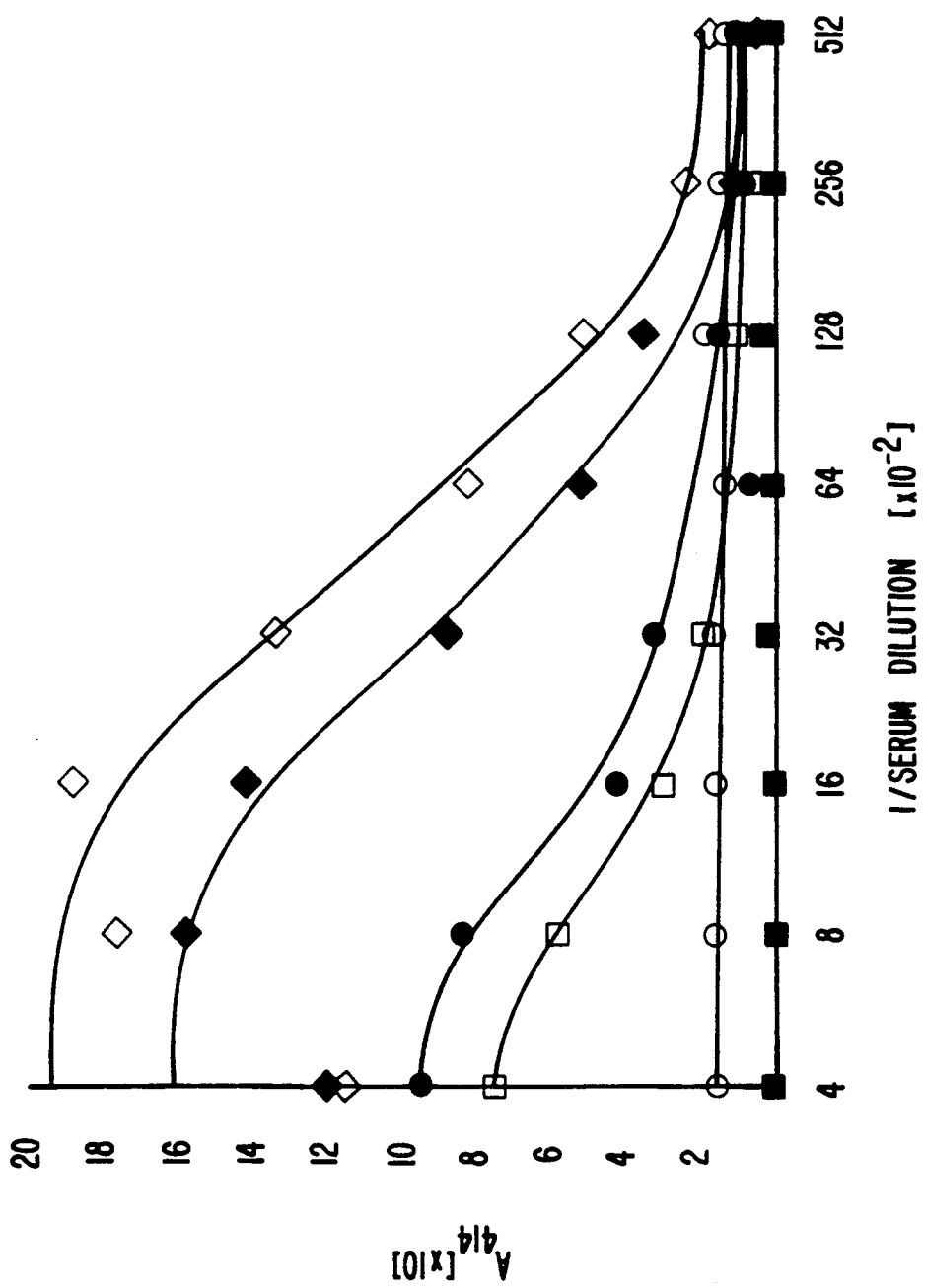

FIG. 4 is a graph illustrating immunoreactivities of oligoclonal antibodies raised to synthetic polypeptides corresponding in amino acid residue sequence (i) to positions 139 through 155 of the predicted sequence of the simian sarcoma virus transforming protein denominated p28$^{sis}$ [Devare et al., *Proc. Natl. Acad. Sci. USA*, 80, 731–735 (1983)] identified hereinafter as polypeptide (c) and as PDGF 2(73–89), and (ii) to residues 2 through 18 of the predicted amino acid residue sequence of the avian myeloblastosis virus oncoprotein [Rushlow et al., *Science*, 216, 1421–1423 (1982)] identified hereinafter as polypeptide (d). The synthetic polypeptides conjugated to keyhole limpet hemocyanin (KLH) were used to immunize mice as is discussed generally in the Materials and Methods section.

To test the specificity of oligoclonal antibody-containing sera so prepared, 250 nanograms of unconjugated polypeptide or 500 nanograms of KLH were dried onto the bottoms of microtiter wells and fixed with methanol as described by Niman and Elder, in *Monoclonal Antibodies and T Cell Products*, Katz ed., CRC Press, Boca Raton, Florida, pp. 23–51 (1982). The remaining portions of the wells were blocked against non-specific protein adsorption using 3% bovine serum albumin (BSA) and a 4 hour incubation period at 37 degrees C.

Into each well of the microtiter plate was instilled 25 microliters each of two-fold dilutions of immunized mouse sera, starting with a dilution of 1:400, using tissue culture medium supplemented with 10% fetal calf serum and were incubated with the BSA-blocked polypeptide or KLH for 16 hours at 25 degrees C. After washing 10 times with distilled water, 25 microliters of rabbit anti-mouse kappa antibody (Litton Bionics Inc., Kensington, Maryland) diluted 1:500 with 1% BSA in phosphate-buffered saline (PBS) were added and incubated for 2 hours at 37 degrees C. After an additional 10 washings with distilled water, 25 microliters of goat anti-rabbit IgG conjugated to glucose oxidase and diluted 1:500 with 1% BSA in PBS were added and incubated for 1 hour at 37 degrees C.

The amount of glucose oxidase so bound was determined by addition of 50 microliters of a solution containing 100 micrograms/milliliter of ABTS dye (Boehringer-Mannheim) in the presence of 1.2% glucose and 10 micrograms/milliliter of horseradish peroxidase in 0.1 molar phosphate buffer having a pH value of 6.0. The optical densities of the solutions so prepared are read at 414 nanometers using a Titertech microscanner (Flow Laboratories Inc., Inglewood, California).

Bindings exhibited by oligoclonal antibodies in sera raised to the sis-related and myb-related polypeptides are shown by open and closed symbols, respectively. The antibody antigens are: sis-related polypeptide (c) (O,●); myb-related polypeptide (d) (□,■); and KLH (◊,♦).

Figure 5:
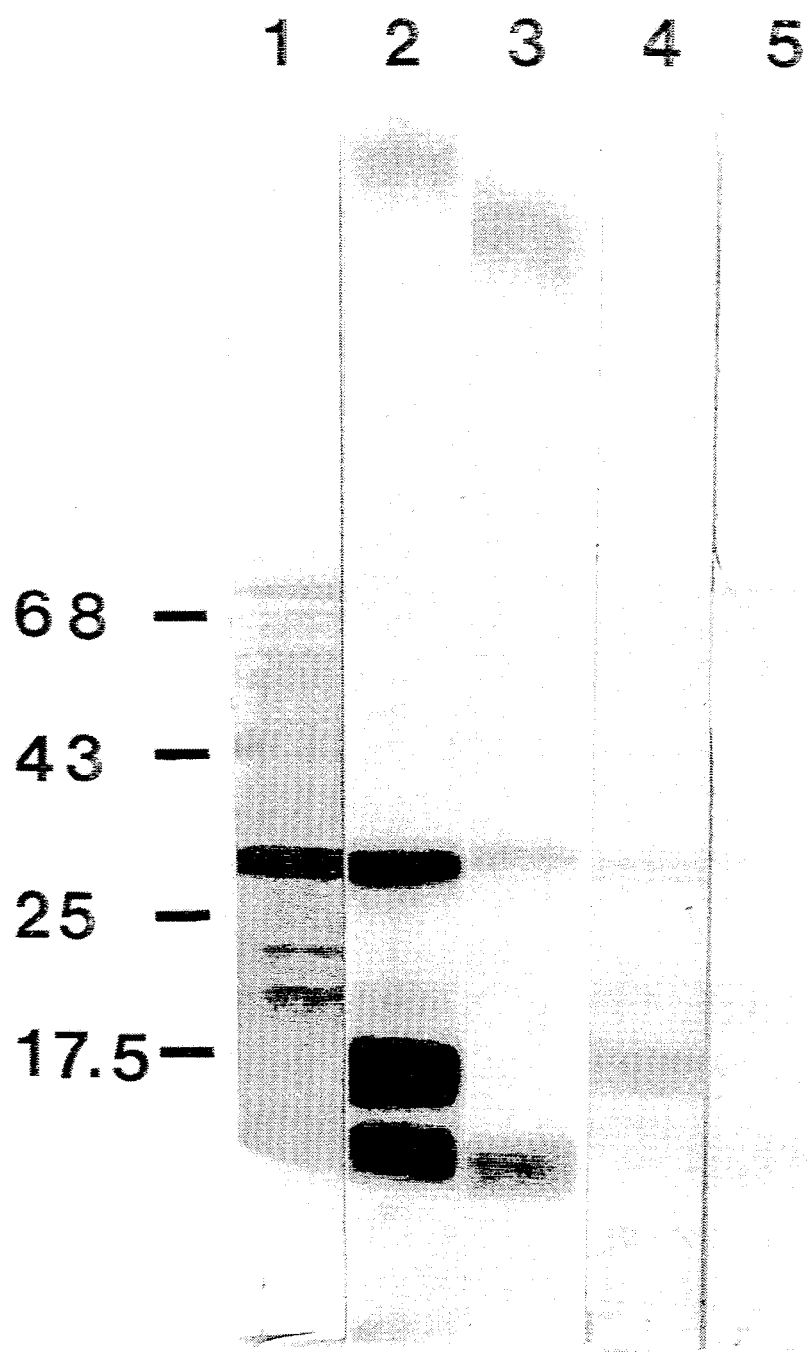

FIG. 5 is a photograph of an autoradiograph illustrating an immunological assay for detecting the presence of non-reduced and reduced platelet-derived growth factor (PDGF) using mouse anti-sera containing oligoclonal antibodies (receptors) induced by synthetic polypeptides (c) and (d) as probes. PDGF extract was purified from outdated platelets as described in the Materials and Methods section.

Purified PDGF extract from approximately 2.5 units of platelets were mixed with a minimal volume of solution containing 0.5% sodium dodecyl sulfate (SDS) and 5 percent of 2-mercaptoethanol. The resulting mixture was boiled for 2 minutes and then electrophoresed therethrough a 5–17 percent polyacrylamide gel. The protein was thereafter electrophoretically transferred to nitrocellulose [Niman and Elder, *Virology*, 123, 187–205 (1982)] that was thereafter cut into strips, following the Western blot procedure.

The nitrocellulose strips so prepared were then treated with a solution containing 3% BSA 0.1% polyoxyethylene (9) octyl phenyl ether (Triton ® X-100, Rohm and Haas Company, Philadlephia, PA) in PBS to inhibit non-specific protein binding. 4 Milliliters of mouse anti-serum diluted 1:200 were then incubated with the nitrocellulose strips.

After washing 3 times with a solution of 0.1% Triton ® X-100 in PBS, the nitrocellulose strips were incubated either with $10^6$ counts per minute of $^{125}$I-labeled *Staphvloccous aureus* protein A (lanes 2 and 3), or a 1:1000 dilution of peroxidase-conjugated goat anti-mouse serum (Tago, Inc., Burlingame, California), and again washed with 0.1% Triton ® X-100 in PBS. The peroxidase conjugate was developed with a solution containing 0.0009% $H_2O_2$, 0.0025% 3,3'-dimethoxybenzidine dihydrochloride (Eastman-Kodak Co., Rochester, New York) in a 10 millimolar Tris buffer having a pH value of 7.4. The $^{125}$I-labeled strips were developed by exposure on XRP-1 film (Eastman-Kodak Co., Rochester, New York) using Cronex Hi-Plus (E. I. DuPont de Nemours & Co., Wilmington, Delaware) intensifying screens at minus 70 degrees C. for 48 hours.

Lane 1 contains the total protein stained with amido black. The purified platelet extract is shown probed with anti-sera raised to the sis-related polypeptide (c) (lanes 2 and 4) or the myb-related polypeptide (d) (lane 3 and 5) as a negative control. External molecular weight standards based on BSA, ovalbumin, chymotrypsinogen and beta-lactoglobulin are shown on the left.

Figure 6:
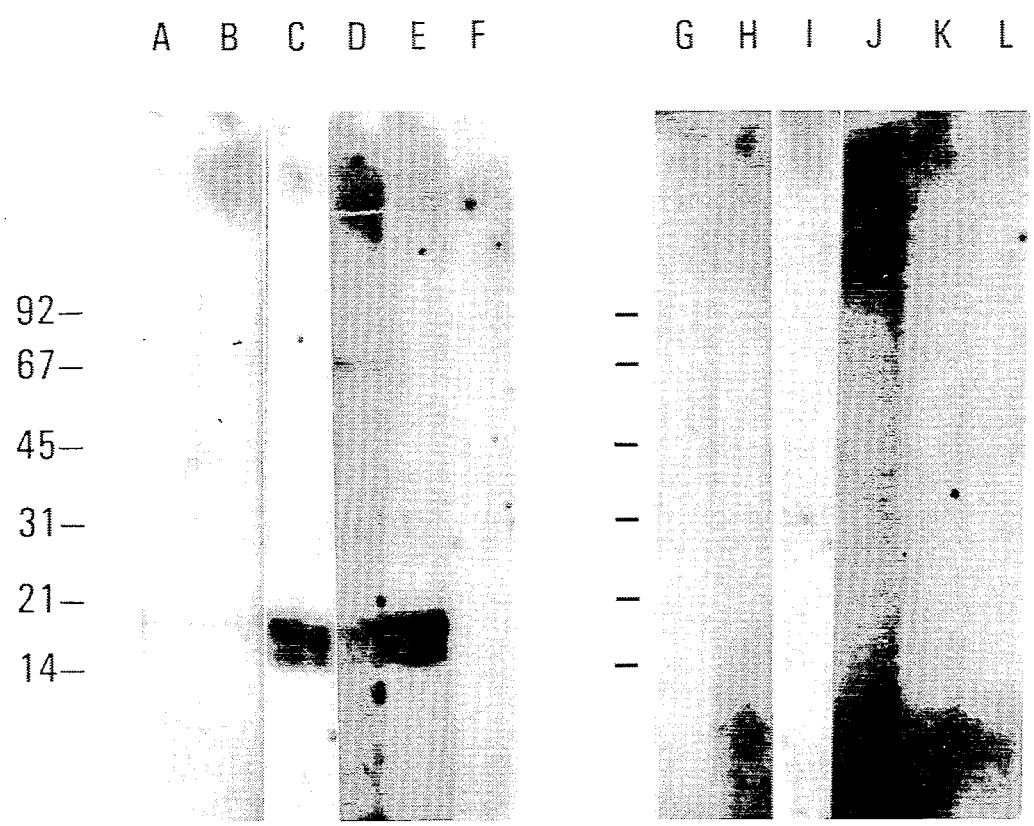

FIG. 6 is a photograph of an autoradiograph illustrating an immunolgical assay for the presence of PDGF following a Western blot procedure similar to that described hereinbefore. PDGF was boiled in the presence (lanes A-F) or absence (lanes G-L) of 10 percent 2-mercaptoethanol prior to electrophoretic protein separation, following the procedures described in Niman, *Nature*, 307, 180–183 (1984). Two oligoclonal antibody-containing antisera induced by the amino-terminal twelve amino acid residues of PDGF-1 [denominated PDGF-1(1–12)] were used in lanes A and G, and lanes B and H. Two oligonal antibody-containing antisera induced by a polypeptide from a central portion of PDGF-2 [denominated PDGF-2(73–89) and polypeptide (c)] that corresponds to the amino acid residue sequence at positions 139 through 155 of p28$^{sis}$ were used in lanes D and J, and in lanes E and K. Oligoclonal antibody-containing antisera induced by the amino-terminal seventeen residues of PDGF-2 [denominated PDGF-2(1–17)] and by the twenty residues of PDGF-2 located 36–16 residues from the carboxy-terminus [denominated PDGF-2(126–145)], corresponding to the sequence at positions 192 through 211 of p28$^{sis}$, were used in lanes C and I, and lanes F and L, respectively. Antibody binding to the proteins was visualized using rabbit anti-mouse IgG$_1$ followed by $1.0^6$ cpm $^{125}$I-labeled *Staphylococcus aureus* protein A as described in Niman, supra, and in the Materials and Methods section hereinafter.

Figure 7:
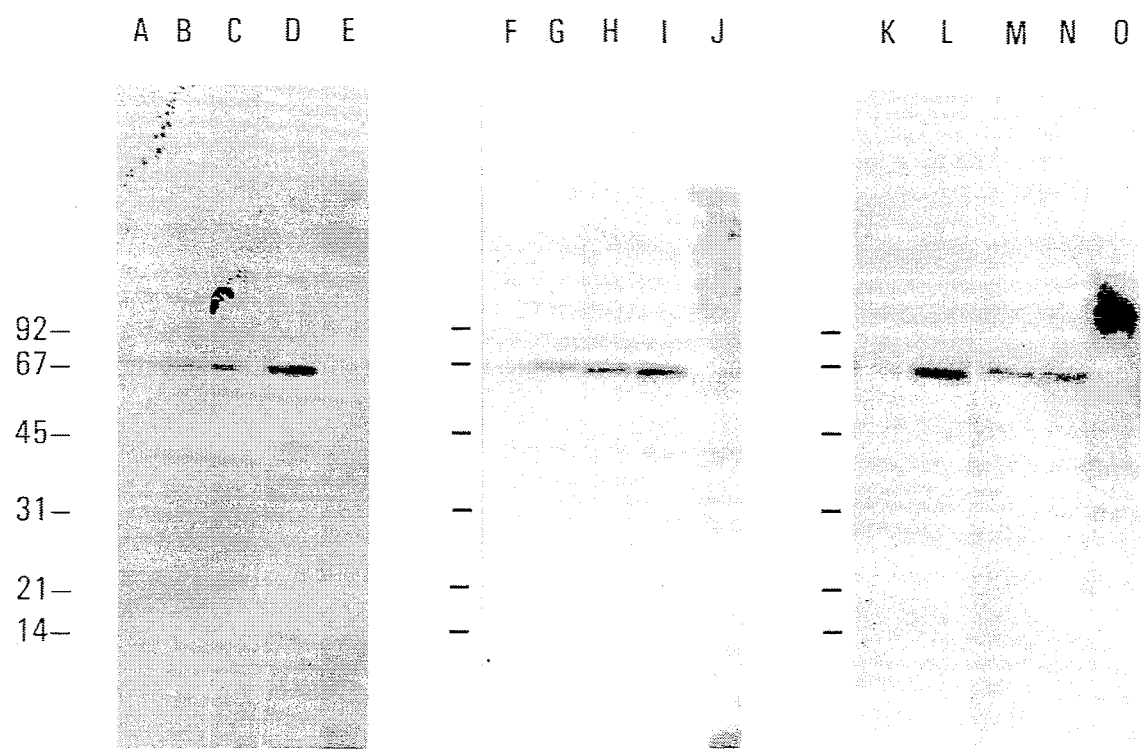

FIG. 7 is a photograph of an autoradiograph illustrating an immunological assay for the presence of a 70,000 dalton protein in three cell lines using a Western blot procedure. An extract from approximately $10^6$ cells per lane from each of SSV-transformed NIH 3T3 cells, (lanes A-E), TRD1 cells (a spontaneously transformed Balb/3T3 cell line)(lanes F-J) and MSTF cells [a mink lung line (CCL64) productively infected with FeLV-B and the Snyder-Theilen strain of FeSV] (lanes K-O) was transferred to nitrocellulose sheets following a Western blot procedure. Oligoclonal antibody-containing antisera induced by PDGF-1(1–12) were used in lanes A-C, F-H and K-M. Oligoclonae antibody-containing antisera induced by PDGF-2(73–89) were used in lanes D,E,I,J,N and O. The antisera were incubated with 100 micrograms of polypeptides PDGF-1(1–12) (lanes A,D,F,I,K and N), PDGF-2(1–17) (lanes B,G and L) and PDGF-2(73–89) (lanes C,E,H,J,M and O) prior to being immunoreacted with the transferred cell extracts. Proteins were visualized as described for FIG. 6.

Figure 8:
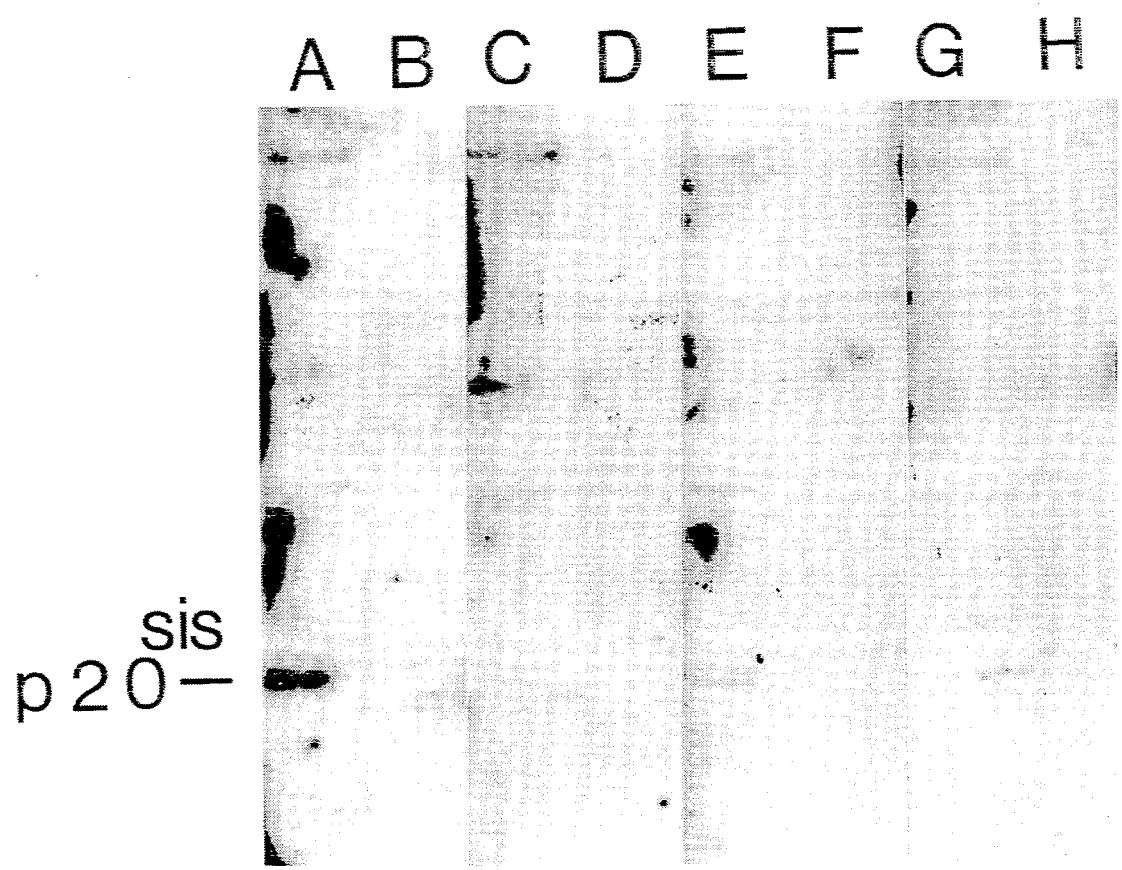

FIG. 8 is a photograph of an autoradiograph illustrating an immunological assay for the presence of $p20^{sis}$ in culture media separately conditioned by SSV-transformed normal rat kidney and normal rat kidney (NRK) cells.

Proteins from concentrated media, equivalent to 25 milliters of non-concentrated media, conditioned by SSV-transformed cells (lanes A,C,E and G) or NRK cells (lanes B,D,F and H) were separated and transferred to nitrocellulose following the Western blot procedure. The transferred proteins were then admixed with oligoclonal antibody-containing antisera induced by PDGF-2(1–17) (lanes A-D) and PDGF-2(73–89) (lanes E-H). Sera were incubated with 100 micrograms of polypeptides PDGF-2(73–89) (lanes A,B,G and H) and PDGF-2(1–17) (lanes C,D,E and F) prior to being immunoreacted with the transferred proteins. Immunoreactions were visualized as described for FIG. 6. The marker "$p20^{sis}$" at the eft side of FIG. 8 indicates the position of $p20^{sis}$.

Figure 9:
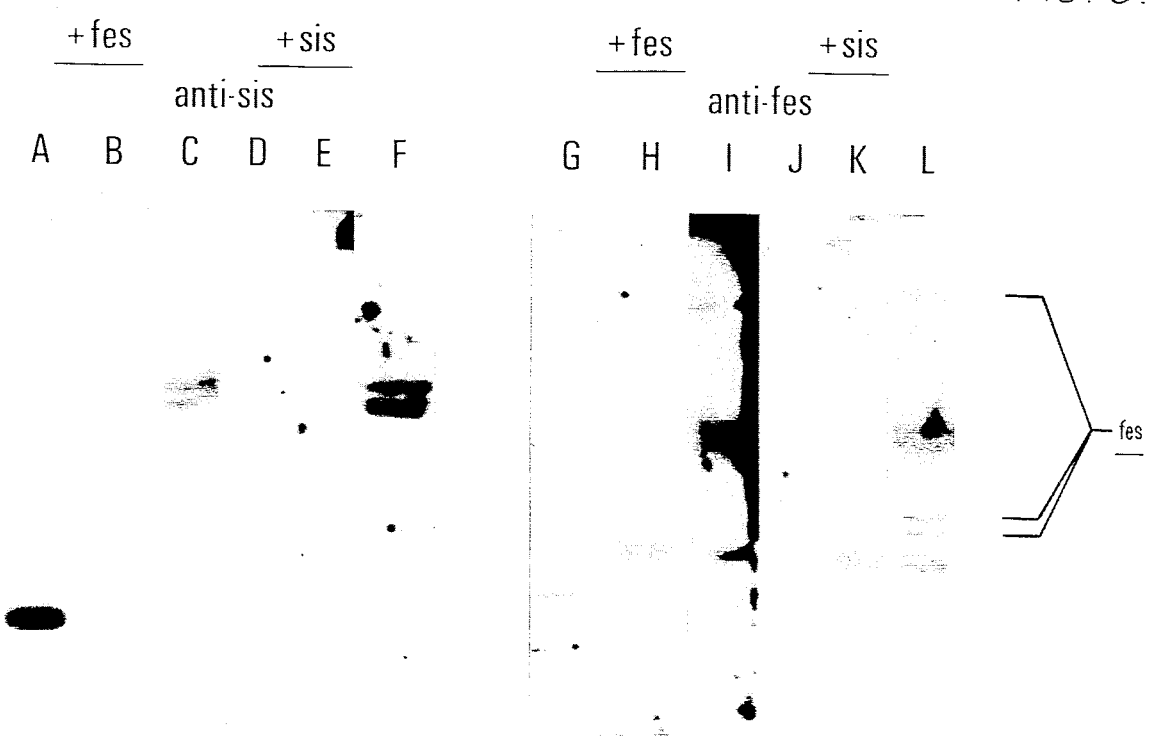

FIG. 9 is a photograph of an autoradiograph illustrating an immunulogical assay for the presence of proteins encoded by or related to sis and fes antisera in urine from human cancer patients. The liquid body sample in this assay was urine concentrate, obtained as described in the Materials and Methods section. The concentrated urine was electrophoresed into 5–17% polyacrylamide gel and then electrophoresed onto nitrocellulose.

Urine from three donors was concentrated 200-fold, dialyzed and 20 microliters of each concentrate were electrophoresed and the proteins therein transferred to nitrocellulose as described before. These three donors had a rectal tumor (lanes A,D,G and J), a liver tumor (lane B,E,H and K) and a cholongiocarcinoma (lanes C,F,I and L). An oligoclonal receptor-containing antiserum induced by the sis-related polypeptide PDGF-2(73–89) that had been preincubated with the immunizing polypeptide was used in lanes D-F, while the same antiserum that had been preincubated with the fes-related polypeptide corresponding to the sequence located at positions 744–759 of the v-fes$^{ST}$ oncoprotein was used in lanes A-C. Similarly, an oligoclonal receptor-containing antiserum induced by the above fes-related polypeptide that had been preincubated with the immunizing polypeptide was used in lanes G-I, while the same antiserum that had been preincubated with the above sis-related polypeptide was used in lanes J-L. Immunoreaction (binding) between the oligoclonal receptors and the proteins was visualized as described for FIG. 6. The positions of the sis- and fes-related proteins detected in the urine concentrates are indicated on the left and right margins by the markers "sis" and "fes", respectively.

Figure 10:
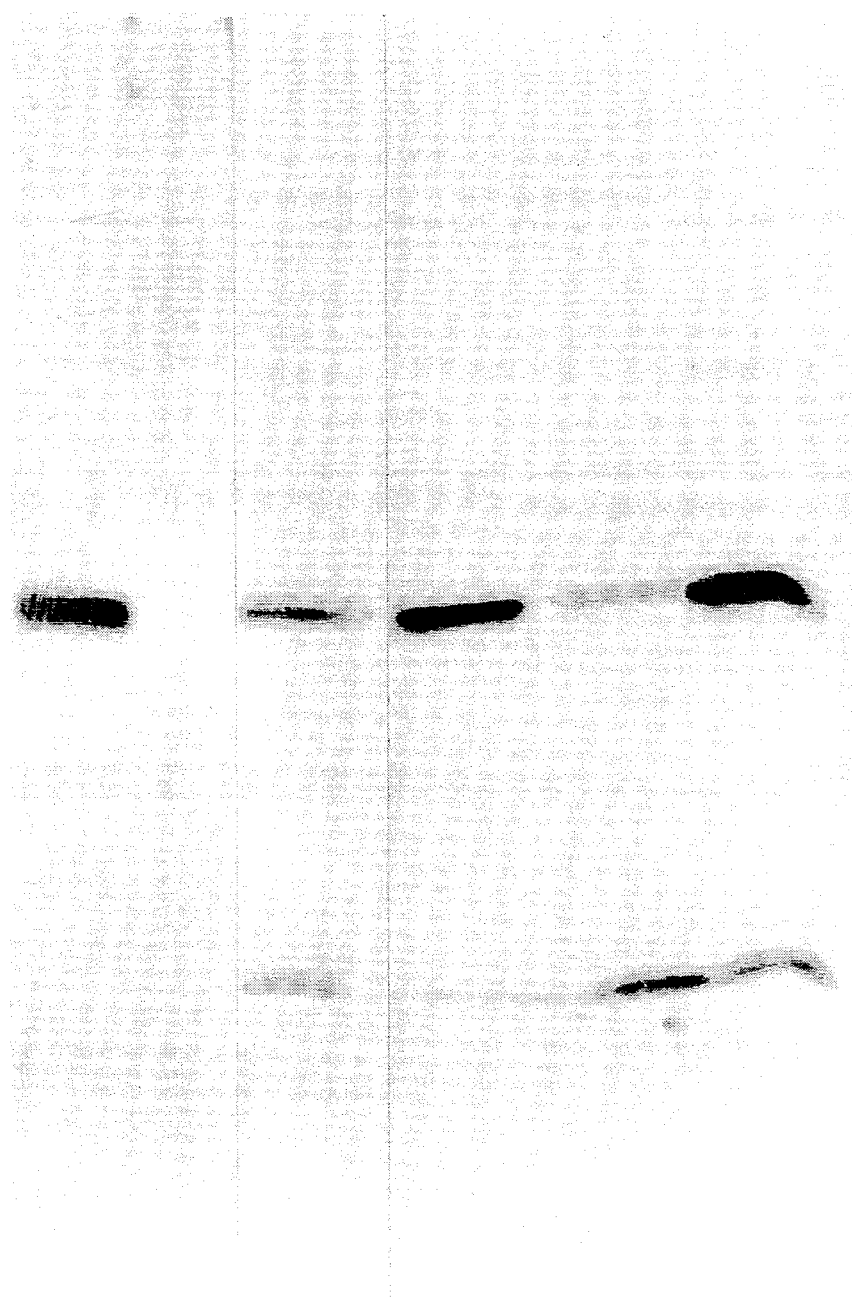

FIG. 10 is a photograph of an autoradiograph illustrating an immunological assay for the presence of ras-related proteins in urine.

Urine was concentrated 250-fold (lanes A and B), 35-fold (lane C), 70-fold (lane D), 75-fold (lane E) and 325-fold (lane F). The urine was dialyzed, 20 microliters of each concentrate were electrophoresed and the proteins therein were transferred to nitrocellulose as described before.

The donors had been diagnosed as normal (lanes A, B and F), or as having one of the following conditions: 38 weeks pregnant (lane C), lymphoma (lane D) and colon carcinoma (lane E). The same normal patient provided the urine samples that were collected 14 days apart and were used in lanes A, B and F.

All urine samples were assayed using 10 microliters of anti-ras ascites fluid incubated with residues 97–118 of the polypeptide $p21^{ras}$ that had been preincubated with residues 744–759 of the polypeptide fes$^{ST}$ (lane A); residues 97–118 of the polypeptide ras$^{Ha}$ (lane B); or residues 139–155 of the polypeptide v-sis (lanes C-F). Immunoreaction (binding) between the oligoclonal receptors and the proteins was visualized as described for FIG. 6. The position of the ras-related proteins detected in the urine concentrates are indicated on the left margin by the marker "ras".

The protein detected that is related to the ras oncogene is detected by a monoclonal antibody secreted by the hybridoma denominated ATCC No. HB 8679 that was raised to a ras-related synthetic peptide. This protein of approximately 55K daltons was detected in Lane A and the activity was blocked by a preincubation with the immunizing peptide (Lane B). Urine collected from the same normal individual contained the same protein two weeks later (Lane F). This protein has been detected in the urine of a pregnant patient (Lane C) and of a cancer patient (Lane D and E).

Figure 11:
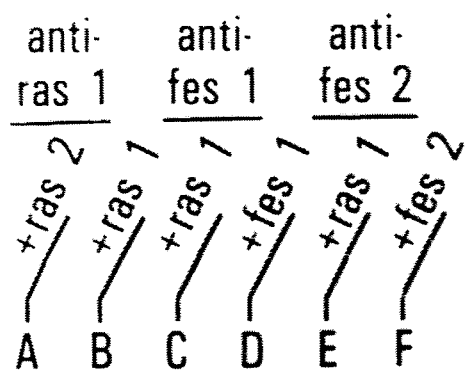
Figure 11:
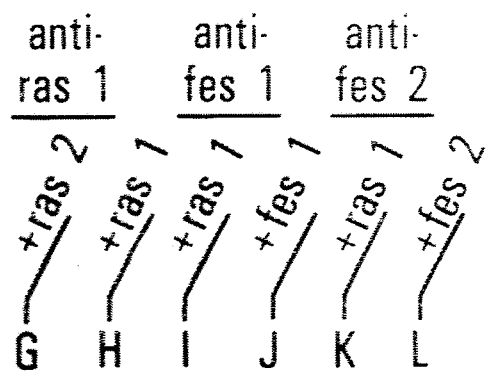
Figure 11:

FIG. 11 is a photograph of an autoradiograph illustrating an immunological assay for the presence of a 23k dalton protein in three cell lines using a Western blot procedure. The lanes of the Figure each contained an extract from about $10^6$ cells per lane from mink lung cell line transformed by the Snyder-Thielen strain of mink lung line sarcoma virus (MSTF) cells (Lanes A-F) or from uninfected MSTF cell line CCL64 (Lanes G-L). The respective cell extracts were transferred from polyacrylamide gel, onto nitrocellulose sheets, followed by a Western blot procedure.

The extracts were assayed using antisera raised to a polypeptide corresponding to residues 97–118 of $p21^{ras}$ ("ras-1"; Lanes A, B, G, H) that had been preincubated with a polypeptide corresponding to residues 5–16 of v-ras$^{HA}$ ("ras-2"; Lanes A,G) or with a polypeptide corresponding to residues 97–118 of $p21^{ras}$ ("ras 1"; Lanes B,H).

The same cell extracts were assayed with antisera raised to polypeptides corresponding to residues 529–540 of p 85-fes ("fes-1"; Lanes C,D,I,J) or to residues 744–759 of p 85-fes ("fes-2"; Lanes E,F,K,L). The antisera were preincubated with the fes-1 polypeptide (Lanes D,J), with the fes-2 polypeptide 744–759 (Lanes F,L), or with the ras-1 polypeptide (Lanes C,E,I,K) prior to being immunoreacted with the transferred cell extracts. Proteins were visualized as described for FIG. 6.

Figure 12:

FIG. 12 is a photograph of an autoradiograph illustrating an immunological assay for the presence of a secreted protein in supernatants from spontaneously transformed mouse 3T3 cell line TRD-1 (Lanes A,B) or a human T-24 bladder carcinoma line (Lanes C,D). The supernatants were assayed for presence of secreted fes-related protein.

The cell lines were grown in the absence of serum and collected after 48 hours of growth. 35 microliters of 1500:1 concentration of T-24 cell line supernatant or 1000:1 concentration of TRD-1 cells were electrophoresed into a polyacrylamide gel, and then transferred onto nitrocellulose.

Mouse antisera to v-fes$^{ST}$ synthetic polypeptide corresponding to residues ("fes-2") 744–759 of p85$^{fes}$ ("fes-2") were utilized for the assay. The antisera were preincubated with a synthetic polypeptide corresponding to residues 519–530 of v-fes$^{ST}$ ("fes-1"; Lanes A and B), or with the fes-2 polypeptide used to raise the antisera (Lanes B and D).

The antisera were then immunoreacted with the transferred cell supernatant. Proteins were visualized as described for FIG. 6.

Figure 13:
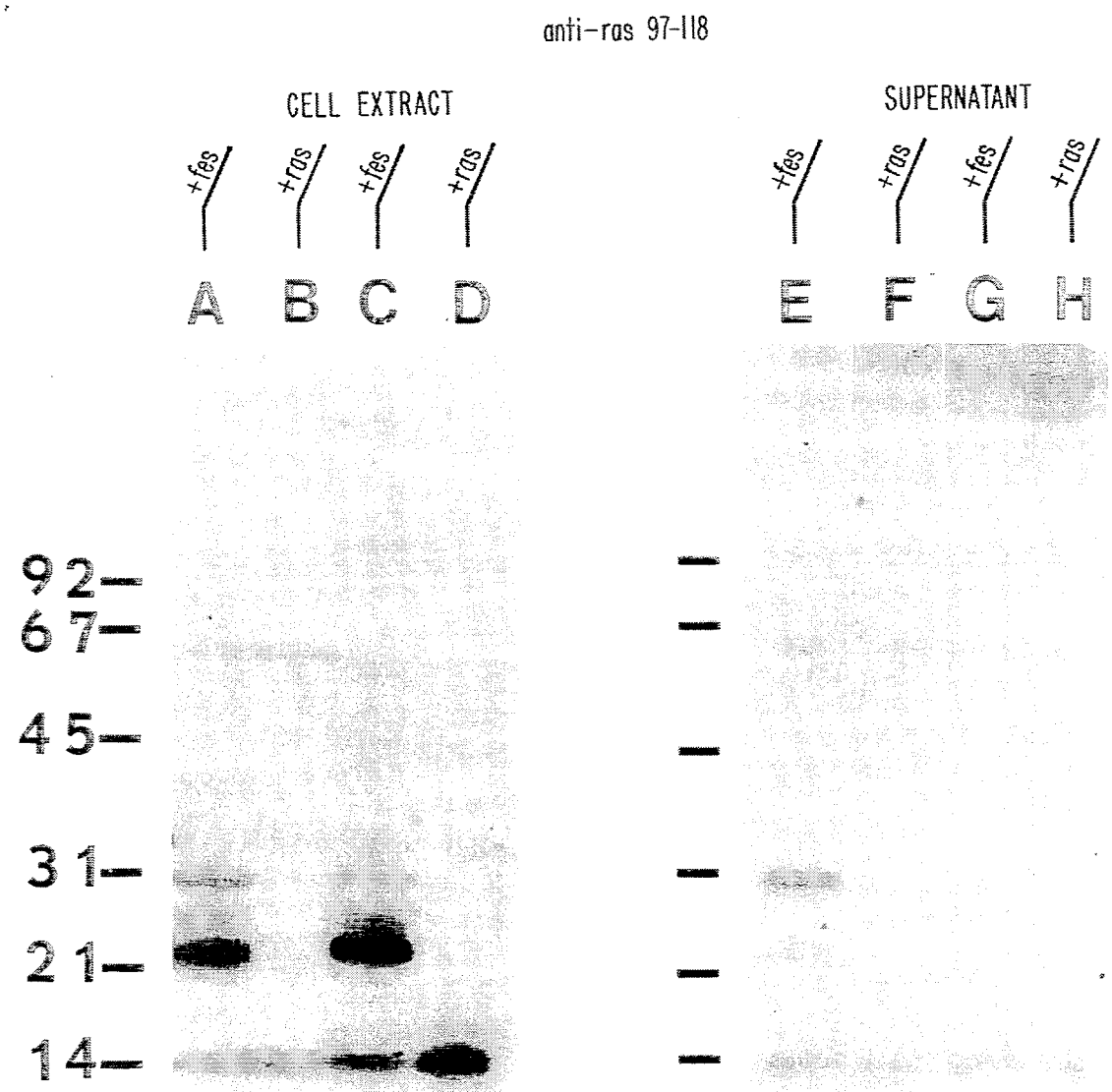

FIG. 13 is a photograph of an autoradiograph illustrating an immunological assay for the presence of a ras related protein in a cell extract using a Western blot procedure.

A cell extract of approximately 10$^6$ spontaneously transformed mouse 3T3 cells was used in Lanes A-D. 35 microliters of a 1500-fold concentration of 48 hour supernatants from mouse 3T3 TRD-1 cells were used in Lanes E-H. The proteins of the supernatants were electrophoresed in a polyacrylamide gel, and then transferred onto nitrocellulose.

Oligoclonal antibody-containing antisera to v-ras$^{HA}$ were preincubated with an unrelated fes polypeptide (Lanes A,C,E,G) or the ras polypeptide used for the immunizations. (Lanes B,D,F,H). Proteins were visualized as described in FIG. 6.

FIGS. 14, 15, and 16 are tables showing amino acid sequences of three conserved regions of oncoproteins that have protein kinase activity. Those regions are denominated as "CONSERVED KINASE REGION" 1, 2 and 3, respectively, in FIGS. 14, 15 and 16. The oncogene encoding an oncoprotein having protein kinase activity is designated by its usual symbol in the left-hand column. The middle column identifies the location in the oncoprotein polypeptide sequence, from the amino-terminus, of the conserved amino acid residue sequence. The right-hand column shows the amino-acid residue sequences, from left to right and in the direction from amino-terminus to carboxy-terminus, of those conserved regions. The amino acid residue sequences are also the sequences of polypeptides useful as immunogens for inducing production of the monoclonal receptors of this invention.

DETAILED DESCRIPTION OF THE INVENTION

The present invention contemplates monoclonal receptor molecules to oncoprotein ligands, to a general method of inducing or raising such receptors, and to products and methods that utilize those receptors. Terms used frequently herein are defined as follows:

Receptor - A "receptor" is a biologically active molecule that binds to a ligand. The receptor molecules of this invention are intact or substantially intact antibodies or idiotype-containing polyamide portions of antibodies. Biological activity of a receptor molecule is evidenced by the binding of the receptor to its antigenic ligand upon their admixture in an aqueous medium, at least at physiological pH values and ionic strengths. Preferably, the receptors also bind to the antigenic ligand within a pH value range of about 5 to about 9, and at ionic strengths such as that of distilled water to that of about one molar sodium chloride.

Idiotype-containing polypeptide portions (antibody combining sites) of antibodies are those portions of antibody molecules that include the idiotype and bind to the ligand, and include the Fab and F(ab')$_2$ portions of the antibodies. Fab and F(ab')$_2$ portions of the antibodies are well known in the art, and are prepared by the reaction of papain and pepsin, respectively, on substantially intact antibodies by methods that are well known. See for example, U.S. Pat. No. 4,342,566 to the Theofilopolous and Dixon. Intact antibodies are preferred, and will be utilized as illustrative of the receptor molecules contemplated by this invention.

Monoclonal receptor - A "monoclonal receptor" (Mab) is a receptor produced by clones of a single cell called a hybridoma that secretes but one kind of receptor molecule. The hybridoma cell is fused from an antibody-producing cell and a myeloma or other self-perpetuating cell line. Such receptors were first described by Kohler and Milstein, Nature, 256, 495–497 (1975), which description is incorporated by reference.

Oligoclonal receptor - An "oligoclonal receptor" is a receptor that is induced by and binds to more than one epitope on a polypeptide of moderate length such as about 7 to about 40 or more preferably about 10 to about 30 amino acid residues long. Oligoclonal receptors are usually a mixture of receptors produced by more than one cell. Oligoclonal receptors so produced are usually more epitopically specific in their binding than are the polyclonal receptors raised to whole protein molecules that can have epitopic regions throughout the length of the protein chain or chains. Animals immunized with the polypeptides useful herein produce sera containing oligoclonal receptors (antibodies).

Ligand - A "ligand" is the protein or polypeptide to which a receptor of this invention binds.

Corresponds - The term "corresponds" as used herein in conjunction with amino acid residue sequences means that the amino acid residue sequence of a first polypeptide or protein is sufficiently similar to the amino acid residue sequence contained in a second polypeptide or protein so that receptors raised to the first (e.g., an antigenic synthetic polypeptide) immunologically bind to the second (e.g., an oncoprotein) when the two are admixed in an aqueous composition.

The epitope-containing amino acid residue sequences of the corresponding first and second polypeptides or proteins are most preferably identical. However, changes, preferably conservative, in amino acid residues, and deletions or additions of residues, within the epitope may be made and still permit the cross-reaction of a receptor to the first polypeptide or protein with the second, as is known. Conservative changes in amino acid residues are well known, and include exchanges of residues between lysine (Lys; K) and arginine (Arg; R), between aspartic acid (Asp; D) and glutamic acid (Glu; E), between leucine (Leu; L) and isoleucine (Ile; I) and the like.

The polypeptides useful herein are frequently described as having an amino acid residue sequence that corresponds to a portion of amino acid residue sequence of a protein. Such polypeptides preferably only contain amino acid residues that correspond identically, in addition to terminal residues such as Cys residues utilized for binding or linking the polypeptide to a carrier. Additional amino acid residues that do not correspond to residues in the protein may also be present at polypeptide terminii, but the use of such residues, while contemplated herein, is usually wasteful, and is not preferred.

Similarly, proteins are described as having an amino acid residue sequence to a portion of which the amino acid residue sequence of a polypeptide corresponds. This terminology is intended to imply the same relationship between the polypeptide and protein discussed hereinabove.

The full names for individual amino acid residues are sometimes used herein as are the well-known three-letter abbreviations. The one-letter symbols for amino acid residues are used most often. The Table of Correspondence, below, provides the full name as well as the abbreviations and symbols for each amino acid residue named herein.

| Table of Correspondence | | |
|---|---|---|
| Amino acid | Three-letter abbreviation | One-letter symbol |
| Alanine | Ala | A |
| Arginine | Arg | R |
| Asparagine | Asn | N |
| Aspartic acid | Asp | D |
| Asparagine + aspartic acid | Asx | B |
| Cysteine | Cys | C |
| Glutamine | Gln | Q |
| Glutamic acid | Glu | E |
| Glutamine + glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

(A. L. Lehninger, Biochemistry; Worth Publishers, Inc., N.Y., N.Y., 1970)

I. PRODUCTION OF MONOCLONAL RECEPTORS

As noted previously, the present invention contemplates monoclonal receptor molecules that bind to an immunogenic polypeptide of moderate length, e.g., about 7 to about 40 residues and preferably about 10 to 30 residues, as well as binding to a protein molecule ligand, a portion of whose amino acid residue sequence corresponds to the amino acid residue sequence of that polypeptide. The monoclonal receptors of this invention are raised or induced by use of an immunogenic polypeptide or conjugate of that polypeptide linked to a carrier; the immunogenic polypeptide containing an amino acid residue sequence of moderate length corresponding to a portion of the amino acid residue sequence of the protein molecule ligand.

Epitopic localization of monoclonal antibodies poses technical problems. Monoclonal antibodies to the entire bacterial gene products can be produced with two different types of immunogens, native or denatured. Use of native protein poses the most serious technical problems regarding purification and subsequent epitope mapping. The chief advantage of using a native protein is the production of monoclonal antibodies that block the biological function of the target protein.

The oncogene product produced in bacteria is typically not structurally the same as the gene product synthesized in higher organisms. Direct evidence for this difference is provided by analysis of the sis gene product. In mammalian cells the $p28^{sis}$ is rapidly cleaved into $p20^{sis}$. In contrast, bacterial $p28^{sis}$ is not cleaved nor does it form a dimer. Indirect evidence for differences between other oncogene products produced in bacteria or avian cells is provided by the observation that monoclonal antibodies raised against the *E. coli*-produced protein product bind much more efficiently to the immunogen than to the protein synthesized in transformed chicken cells, even though the immunogen was denatured.

Thus, although purification of denatured protein is technically easier, the resulting antisera may recognize conformations unique to the bacterial gene product. This observation poses serious technical difficulties for epitope mapping studies.

Approaches for defining the epitope of the antibodies employ protein fragments generated by partial proteolysis or expression of subgenomic fragments. Although mapping of epitopes using protein fragments was first demonstrated by Niman and Elder, 1980, only an approximation of the binding sites could be made even when several digests were assayed with a large panel of monoclonal antibodies. Thus, immunization even with protein fragments limits the definition of the binding site. Furthermore, there is no guarantee that regions of interest will induce monoclonal antibodies.

In contrast, immunization with appropriate polypeptides of known amino acid residue sequence as carried out herein, assures a production of antibodies (receptors) that immunoreact with well defined regions; i.e., regions that correspond to the sequences of the immunizing polypeptides.

Mapping of epitopes suggests that changing the epitope by one amino acid may produce markedly different reactivities, while other studies show that cross-reactivities are obtained when one or more amino acid residues are different within the epitope. Furthermore, immunization of the same strain of mouse with the same synthetic polypeptide may produce different reactivities detected in the serum.

Hybridomas produced with synthetic polypeptides also produce monoclonal receptors that react with the intact protein under a variety of reaction conditions because the recognition is largely conformationally independent. Therefore, Western blot, dot blot, fixed cells, and fixed tissues and body fluids such as amniotic fluid, and urine, either concentrated or as obtained, can be assayed as well as native proteins. Furthermore, the known, precisely defined amino acid residues in the epitope allow isolation of antibodies that can distinguish single amino acid changes, therefore providing a means of determining the significance of limited changes in conserved regions of related proteins.

Monoclonal antibodies against synthetic polypeptides also provide a means of mapping sites of protein interaction. Differential coprecipitations of molecules associated with the pp60$^{src}$ have been reported, suggesting identification of regions of src proteins that are involved in such interactions.

Thus, inducing the production of monoclonal antibodies (receptors) with an immunogenic synthetic polypeptide assures isolation of antibodies that immunoreact with domains defined by the sequence of the immunizing polypeptide does not require complex methodologies for isolation of the corresponding immunogenic oncoprotein or the identification of that oncoprotein's epitopic site, and produces receptors that recognize the oncogene product in a conformation independent manner, all of which broaden the application of such receptors for a variety of studies.

It was noted previously that although animal host protection has been shown to be possible by the use of immunogenic polypeptides as the active agents in vaccines, the ability to utilize such immunogenic polypeptides to produce high yields of hybridoma tissue cultures that secrete avid monoclonal antibodies (Mabs) was not heretofore thought a likely possibility. Since each Mab is derived from a single cell that produces only one specificity, the ratio of the number of clones producing anti-polypeptide antibodies that also recognize the intact protein molecule, to the total number of polypeptide recognizing clones can provide a reasonable estimate of the true confirmational frequency of the polypeptide.

The results described herein are contrary to the before-mentioned stochastic model, and the frequency for the moderate-length polypeptides used herein assuming a conformation similar to that of the native protein is much higher than was previously expected. The frequency of producing hybridomas whose Mabs recognize both the synthetic polypeptide to which they were raised and the intact molecule is about 4 orders of magnitude (about 10,000) times greater than that predicted by the stochastic theory.

It is also noted that various workers have been utilizing immunogenic polypeptides to raise antibodies that recognize those polypeptides for several decades. In addition, the above referenced Kohler and Milstein article as to the production of monoclonal antibodies was published in 1975. Since that date, 1975, the Arnheiter et al., supra described an attempt to prepare a monoclonal antibody using a polypeptide immunogen. As was previously noted, the Arnheiter et al. results must be viewed as a failure in that those authors required the use of the spleens of three immunized mice and obtained only one IgG type monoclonal antibody that recognized their large, 56-mer polypeptide as well as the protein to whose sequence that polypeptide corresponded.

It is believed that the relative paucity of published reports relating to the preparation of monoclonal receptors prepared from immunogenic polypeptides that recognize both the immunogen and a protein ligand to whose amino acid sequence the immunogenic polypeptide corresponds in part is due to at least two factors. First, the prevalent thought following the stochastic model predicts that few if any such monoclonal antibodies could be prepared. Second, the fact that workers such as Arnheiter et al., above, did not possess a method suitable for the preparation of the monoclonal receptors, inasmuch as the monoclonal receptors of this invention that are raised to polypeptides are prepared differently from monoclonal antibodies prepared to whole proteins.

Thus, to successfully prepare Ig class monoclonal receptors that recognize both the immunogenic polypeptide and the protein ligand to whose amino acid residue sequence that polypeptide corresponds in part, one should follow the steps outlined hereinbelow.

An immunogenic polypeptide alone, or as a conjugate of that polypeptide bound (linked) to a carrier is provided. That polypeptide has an amino acid residue sequence of moderate length, such as about 7 to about 40 amino acid residues, and preferably about 10 to about 30 residues. The amino acid residue sequence of the immunogenic polypeptide corresponds to a portion of the amino acid residue sequence of a protein molecule ligand such as an oncoprotein. While the immunogenic polypeptide can be used by itself as a ligand, it is preferred to use the polypeptide immunogen as a conjugate bound to a carrier such as keyhole limpet hemocyanin (KLH), albumins such as bovine serum albumin (BSA), human serum albumin (HSA), red blood cells such as sheep erythrocytes, tetanus toxoid and edestin, as well as polyamino acids such as poly(D-lysine: D-glutamic acid), and the like.

The immunogenicity and antigenicity of the polypeptide may be tested by binding the polypeptide to a keyhole limpet hemocyanin carrier as a conjugate, and then using the conjugate so prepared to immunize a mouse. The immunizing polypeptide or conjugate is dissolved or dispersed in a physiologically tolerable diluent such as normal saline, phosphate-buffered saline or the like as are well known in the art. An adjuvant, discussed below, is also included in the inolculum used for immunizations.

A useful polypeptide is sufficiently immunogenic and antigenic to produce a 50 percent binding titer of the immunized mouse's oligoclonal receptor-containing anti-serum to the polypeptide that is at least about a 1:400 dilution after three immunizations in a one-month period, each of which immunizations contains at least about ten micrograms, and preferably at least about 50 micrograms, of the polypeptide in the conjugate, and utilizing complete Freund's adjuvant for the first immunization and alum as adjuvant thereafter.

This test procedure need not be carried out prior to the use of a given polypeptide as immunogen, but it is preferable to do so as a pre-screening technique to determine that polypeptides will be useful in preparing the desired monoclonal receptors. Whether used as a pre-screen or not, the polypeptides useful herein as immunogens provide the above titer using the above immunization regimen.

Upon provision of the immunogenic polypeptide, a mammal such as a mouse, rabbit, goat, horse or the like, is hyperimmunized with the immunogenic polypeptide or conjugate of that polypeptide bound to a carrier to provide a hyperimmune serum whose receptor molecules exhibit a 50 percent binding titer to the polypeptide of at least about a 1:400 dilution. Thus, the same animal, e.g., a mouse, in which one may desire to pretest the immunogenicity of the polypeptide may be used for raising the Mabs.

It is particularly preferred that the same animal that is used for a pre-test be used for raising the Mabs. This preference stems from the fact that once the above 50 percent binding titer is achieved, the preparation of hybridomas secreting monoclonal antibodies of the desired specificity using the spleen of that animal as the source of antibody-producing cells is substantially assured, aside from the occurrence of random laboratory mishaps such as contamination of cell cultures or otherwise destroying those cultures.

It is noted that the immunization regimen required to provide a hyperimmune state is a function, inter alia, of the animal type, animal weight, the immunogenicity and amounts of the polypeptide and carrier, if used, the adjuvant, if used and the number of immunizations administered in a given time period, as is known. The above-described regimen for obtaining a 50 percent binding titer dilution of at least about 1:400 provides a hyperimmune state in the test mouse and may be used as a proportionalizable basis for inducing hyperimmune states in other animals. It is further noted that three immunizations are not necessarily required to provide the hyperimmunized state, but for a useful polypeptide, three such immunizations in a one-month period are sufficient to produce that state, or the polypeptide is not sufficiently immunogenic for the high yield production of hybridomas and their monoclonal antibodies of this invention.

The serum oligoclonal receptor molecules so produced in the hyperimmunized animal also bind to the protein molecule ligand, to a portion of which the immunogenic polypeptide corresponds in amino acid residue sequence. Binding assays are described in the Materials and Methods Section hereinafter. It is noted that a pure sample of the protein molecule ligand need not be utilized in these assays but rather, a cell extract or tissue preparation such as a microscope slide containing the protein ligand may be utilized.

The hyperimmunized animal is maintained; i.e., kept alive without administration of further immunizations for a period of at least about 30 days after administration of the immunization that produces a 50 percent binding titer of at least a 1:400 dilution. In other words, the animal is first immunized to provide a hyperimmunized state, and then the hyperimmunization is allowed to recede.

The decline in binding activity typically takes one to about five months for mice. This decline in binding titer is believed to correspond to a period in which primed blast cells become capable of mounting a vigorous response when the immunogen is again introduced.

A booster immunization, as by intravenous injection, using the immunogenic polypeptide or its conjugate is administered to the animal after the period of maintenance is completed, e.g., at least 30 days after the last immunization. Antibody-producing cells, such as spleen cells or lymph cells of the boosted animal are then fused with a myeloma cell line from the same animal type (species) within a period of about three to about five days from the day of booster administration to prepare hybridoma cells. The boost is believed to stimulate the maturation of the blast cells to the point at which those cells secrete nearly optimal amounts of oligoclonal antibodies to the polypeptide.

The SP2/O-Ag14 (ATCC CRL 1581), hypoxanthine-amino pterin-thymidine(HAT)-sensitive, myeloma cell line is preferred for use in fusion with mouse spleen cells, although other cell lines may also be utilized. Details using this HAT line for fusion are given hereinafter in the Materials and Methods Section. The hybridoma cells are thereafter cloned at limiting dilution free from the presence of, or need for, feeder layers or macrophages to reduce overgrowth by non-producing cells, and to provide a selection method for cells which grow readily under in vitro conditions. Such feeder layers may, however, be used.

The hybridoma cells so prepared are then assayed for the production (secretion) of monoclonal receptor molecules that bind to the protein molecule ligand. This ligand is a portion of the protein to which the immunogenic polypeptide corresponds in amino acid residue sequence. Thereafter, the hybridoma cells that produce monoclonal receptor molecules that bind to the protein ligand are cultured further to prepare additional quantities of those hybridoma cells, and the monoclonal receptors secreted by those cells that bind to the protein molecule ligand. Typically, such culturing is done at limiting dilution, e.g., at an average of about one cell per culture-growing well.

In preferred practice, the hybridoma cells that are prepared are also assayed for the production of monoclonal receptor molecules that bind to the polypeptide immunogen as well as to the protein ligand. Thereafter, hybridoma cells that produce monoclonal receptor molecules that bind to both the immunogenic polypeptide and to the protein ligand are those cells that are preferably cultured.

Where samples of the protein molecule ligand are limited, it is convenient to first screen the hybridomas for secretion of monoclonal receptors that bind to the immunogenic polypeptide. Hybridoma clones that exhibit positive binding to that polypeptide are then typically frozen for storage. They are thereafter thawed, and subcloned by limiting dilution for assurance that truly monoclonal antibodies are produced, rather than a plurality of monoclonal receptors being produced from a plurality of different hybridoma cells. Those limiting dilution subcloning cultures are again typically carried out free from feeder layers or macrophages, as such are not necessary.

The hybridoma cells that are ultimately produced may be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid are typically 129xBALB/c mice bred in the mouse colony of the Scripps Clinic and Research Foundation, La Jolla, California. However, when animals other than mice are used for preparation of the hybridomas, that animal type is used for the production of ascites fluid.

As noted previously, it is preferred that the myeloma cell line be from the same species as the receptor. Therefore, fused hybrids such as mouse-mouse hybrids [Shulman et al., *Nature*, 276, 269 (1978)] or rat-rat hybrids [Galfre et al., *Nature*, 277,131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al. eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/O-Ag14 (ATCC CRL 1581), P3 X 63 Ag8U.1 (ATCC CRL 1597), and Y3-Agl.2.3. (deposited at Collection Nationale de Cultures de Microorganisms, Paris, France, number I-078) and P3X63Ag8 (ATCC TIB 9). Myeloma line Sp2/O-Ag14 is preferred for use in the present invention.

The monoclonal receptors of this invention secreted by hybridomas designated S22C06 and S10F03 are particularly preferred monoclonal receptors. Both preferred monoclonal receptors are an IgG1 monoclonal receptors, having kappa light chains, that immunoreact with the immunizing polypeptide and with the fes-related oncoprotein having an amino acid residue sequence corresponding to the sequence of the immunizing polypeptide.

Thus, following the method of this invention it is now possible to produce relatively high yields of monoclonal receptors that bind to or immunoreact with known, predetermined epitopes of protein molecules such as oncoproteins. In addition, once the skilled worker has produced hyperimmune serum containing oligoclonal antibodies that exhibit a 50 percent binding titer of at least about 1:400 to the immunizing polypeptide, that worker may follow the before-mentioned steps, take the spleen from the hyperimmunized animal, fuse its antibody-producing cells with cells of a myeloma line from the same animal type or strain, and be substantially assured that one or more hybridomas produced from that fusion secrete monoclonal receptors that bind to the immunizing polypeptide and to the corresponding protein, such as an oncoprotein. Such results were not heretofore possible.

The above method is useful for preparing hybridomas that secrete monoclonal receptors to substantially any protein molecule ligand. Illustrative of such hybridomas and their monoclonal receptors are those raised to immunogenic polypeptides of moderate length whose amino acid residue sequences correspond to amino acid residue sequences of oncoproteins encoded by oncogenes. Exemplary oncogenes and useful immunogenic polypeptides are shown below followed by the parenthesized, numerical position from the amino-terminus in the oncoprotein sequence to which the polypeptide corresponds wherein the amino acid residue sequences of those polypeptides are given from left to right and in the direction of amino-terminus to carboxy-terminus, and are represented by a formula selected from the group consisting of formulae shown in Table 1, below:

TABLE 1

| Oncogene | Polypeptide Sequence |
|---|---|
| v-fes$^{ST}$* | SDVWSFGILLWETFSLGASPYPNLSNQQTR (693-722) |
|  | IHRDLAARNCLVTEKN (632-647) |
|  | SSGSDVWSFGILLWE (690-704) |
|  | IGRGNFGEVFSG (519-530) |
|  | LMEQCWAYEPGQRPSF (744-759) |
|  | VPVKWTAPEALNYGR (674-688) |
|  | SPYPNLSNQQTR (711-722) |
| v-myb* | RRKVEQEGYPQESSKAG (2-18) |
|  | RHYTDEDPEKEKRIKELEL (94-112) |
| v-sis* | RKIEIVRKKPIFKKATV (139-155) |
|  | RVTIRTVRVRRPPKGKHRKC (192-211) |
| v-ras$^{Ha}$* | YREQIKRVKDSDDVPMVLVGNKC (97-118) |
|  | KLVVVGARGVGK (5-16) |
| v-ras$^{Ki}$* | KLVVVGASGVGK (5-16) |
| T24-ras$^{Hu}$* | KLVVVGAVGVGK (5-16) |
| c-ras$^{Hu}$* | KLVVVGAGGVGK (5-16) |
| c-myc$^{Hu}$* | CDEENFYQQQQQSEL (25-40) |
|  | PAPSEDIWKKFEL (43-55) |
|  | LPTPPLSPSRRSGLC (56-70) |
|  | CDPDDETFIKNIIIQDC (117-133) |
|  | CSTSSLYLQDLSAAASEC (171-188) |
|  | CASQDSSAFSPSSDSLLSSTESSP (208-231) |
|  | APGKRSESGSPSAGGHSKPPHSPLVLKRC (272-300) |
|  | CTSPRSSDTEENVKRRT (342-358) |
|  | AEEQKLISEEDLLRKRLRRQLKHKLEQLRNSCA (408-439) |
| v-mos* | LPRELSPSVDSR (42-53) |
|  | RQASPPHIGGTY (260-271) |
|  | TTREVPYSGEPQ (301-312) |
| v-erb-B | ENDTLVRKYADANAVCQ (25-41) |
|  | LGSGAFGTIYKG (138-149) |
|  | IMVKCWMIDADSRPKF (366-381) |
| PDGF-2* | SLGSLTIAEPAMIAECK (1-17) |
|  | RKIEIVRKKPIFKKATV (73-89) |
|  | RVTIRTVRVRRPPKGKHRKC (126-145) |
| PDGF-1* | SIEEAVPAECKTR (1-12) |

*v-fes$^{ST}$ = Polypeptides from predicted sequences encoded by the fes oncogene of Snyder-Theilen strain of feline leukemia virus. Hampe et al.y Cell, 30, 775-785 (1982).
v-myb = Polypeptides from predicted sequences encoded by the myb gene of avian myeloblastosis virus. Rushlow et al., Science, 216, 1421-1423 (1982).
v-sis = Polypeptides from predicted sequences encoded by sis gene of simian sarcoma virus. Devare et al., Proc. Natl. Acad. Sci. USA, 79, 3179-3182 (1982).
v-ras$^{Ha}$ = Polypeptides from predicted sequences encoded by the ras oncogene of Harvey murine sarcoma virus. Dhar et al., Science, 217, 934-937 (1982).
v-ras$^{Ki}$ = Polypeptides from predicted sequences encoded by the ras oncogene of Kirsten murine sarcoma virus. Tsuchida et al., Science, 217, 937-939 (1982).
T24-ras$^{Hu}$ = Polypeptides from predicted sequences encoded by the ras oncogene of human bladder carcinoma. Reddy et al., Nature, 300, 149-152 (1982).
c-ras$^{Hu}$ = Polypeptides from predicted sequences encoded by the ras oncogene of normal human cells. Reddy et al., Nature, 300, 149-152 (1982).
c-myc$^{Hu}$ = Polypeptides from predicted sequences encoded by the myc oncogene of normal human cells. Colby et al., Nature, 301, 722-725 (1983).
v-mos = Polypeptides from predicted sequences encoded by the mos oncogene of normal human cells. Van Beveren et al., Nature, 289, 258-262 (1981).
PDGF-2 = Polypeptide from sequence encoded by the gene for human platelet-derived growth factor, chain 2. Doolittle et al., Science, 220, 275-277 (1983).
PDGF-1 = Polypeptide from sequence encoded by the gene for human platelet-derived growth factor, chain 1. Doolittle et al., Science, 220, 275-277 (1983).

The homologous polypeptides encoded by the above four ras genes may be conveniently written as one amino acid residue sequence, from left to right and in the direction from amino-terminus to carboxy-terminus, represented by the formula

KLVVVGAR(S,V,G)GVGK wherein the amino acid residues in parentheses are each an alternative to the immediately preceding amino acid residue, "R", in the formula.

Further immunogenic polypeptides useful for inducing the production of monoclonal receptors of this invention are shown in Table 2 below, wherein the oncogene abbreviations and parenthesized positions are as described for Table 1.

TABLE 2

| Oncogene | Sequence |
|---|---|
| sis | DPIPEELYEMLSDHSIRSF (8-26) |
| v-ras$^{Ki}$ | YREQIKRVKDSEDVPMVLVGNKC (96-118) |
| v-ras$^{Ha}$ | YTLVREIRQHKLRKLNPPDESGPGC (157-181) |
| v-ras$^{Ki}$ | YTLVREIRQYRLKKISKEEKTPGC (157-180) |
| v-src | GSSKSKPKDPSQRRRS (2-17) |
|  | LGQGCFGEVWMG (273-284) |
|  | LMCQCWRKDPEERPTF (494-509) |
| v-myb | LGEHHCTPSPPVDHG (159-173) |

Still further useful polypeptides for inducing the production of monoclonal receptors of this invention are the polypeptides whose oncogene, position in the oncoprotein sequence and polypeptide amino acid residue sequences are shown in FIGS. 14, 15, and 16. Those polypeptides correspond to sequence-conserved regions in the well known family of protein kinase oncoproteins, some of whose oncogenes have been previously noted herein.

II. MONOCLONAL RECEPTORS

While the present invention contemplates a large number of monoclonal receptors, five such receptors, intact monoclonal antibodies (Mabs), will be discussed in detail herein as illustrative of the group. The above-discussed test for the immunogenicity and antigenicity of the polypeptide will be discussed thereafter for polypeptides corresponding to additional monoclonal receptors that bind to different oncoproteins.

A. Exemplary Receptors

Five exemplary monoclonal receptors was raised to the v-fes related, 30-mer immunogenic, synthetic polypeptide shown below (polypeptide a), and each also binds to the carboxy-terminal 12-mer polypeptide shown below (polypeptide b), as well as binding to the oncoprotein denominated p85 (85K daltons) encoded by the v-fes gene of ST-FeSV. The amino acid residue sequences of synthetic polypeptides (a) and (b), from left to right and in the direction from amino-terminus to carboxy-terminus, are represented by the formulaes polypeptide a   SDVWSFGILLWETFSLGASPYPNLSNQQTR;
polypeptide b   SPYPNLSNQQTR.

The hybridomas secreting these Mabs were denominated S10F03, S22C06, P43D09, P42C10 and P44E11. Four of the above hybridomas were received at the American Type Culture Collection (ATCC) of Rockville, MD on Aug. 2, 1984, and were given the designations ATCC HB 8596 (S10F03), ATCC HB 8595 (S22C06), ATCC HB 8594 (P43D09), and ATCC HB 8593 (P44E11), respectively.

The hybridoma was raised to the ras 23 mer. immunogenic, synthetic polypeptide (ras) shown below:

YREQIKRVKDSDDVPM VLVGNKC that also binds to the 55K dalton protein encoded by the ras gene of Harvey sequence. The monoclonal antibody recognizes a 23 K dalton protein in all cell lines tested as well as higher molecular weight protein (unpublished observations). An additional hybridoma useful for this invention was received at the ATCC on Dec. 12, 1984 and was given the designation ATCC HB 8679 (1/24E05-SCRF)).

Another hybridoma was raised to the erb-B related, 16-mer immunogenic synthetic polypeptide shown below. The amino acid residue sequence of the synthetic polypeptide, from left to right and in the direction from amino-termius to carboxy-terminus is represented by the formula:

IMVKCWMIDADSRPKF that also binds to oncoprotein encoded by fes, fms, abl, src and fqr oncogenes.

The hybridomas designated S10F03, S22C06, P43D09, P44E11 and 1/24/E05 secrete kappa-light chained, IgG1 monoclonal receptors.

The last-named five hybridomas were prepared from two separate cell fusions. The efficiency of producing hybridomas whose Mabs recognize the immunogenic polypeptide as well as the corresponding oncoprotein molecule ligand for the first preparation was 100 percent; i.e., two Mabs (from S10F03 and S22C06) were produced that recognize the polypeptide, and those two Mabs also recognize the oncoprotein. For the second preparation, the efficiency, calculated similarly was about 20 percent.

Figure 1:
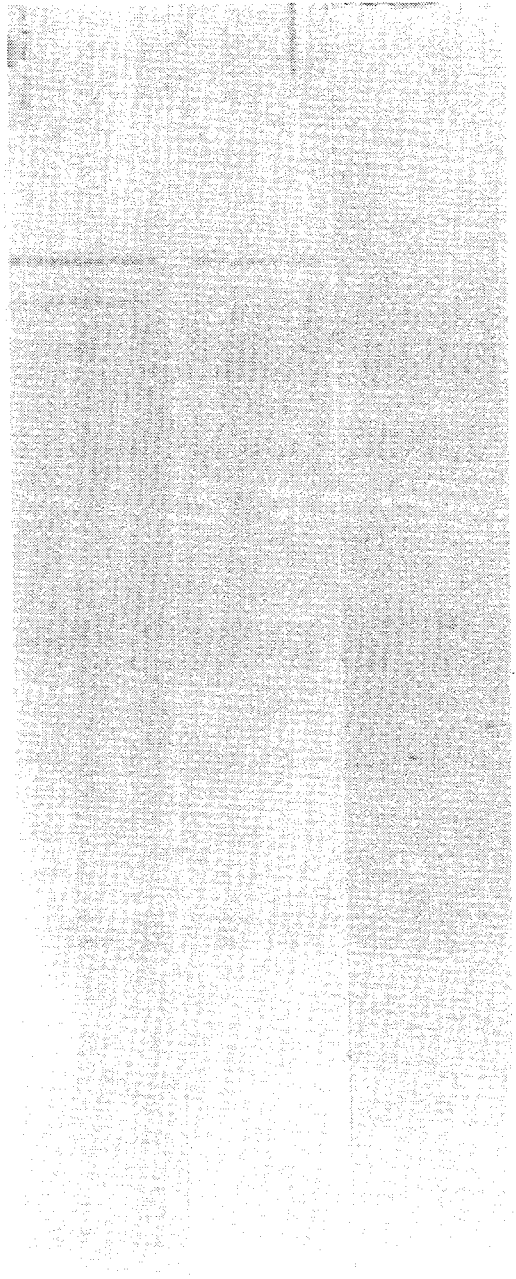
FIG. 1 is a photograph of an autoradiograph illustrating an immunological assay for detecting the presence of the ST-FeSV v-fes oncoprotein. Cell extracts from approximately $10^5$ MSTF cells, a productively transformed mink cell line infected with Snyder-Theilen strain of feline sarcoma virus (ST-FeSV) and feline leukemia virus-B (FeLV-B) [Sen et al., Proc. Natl. Acad. Sci. USA, 80, 1246–1250 (1983)], were electrophoresed onto a 5–17 percent polyacrylamide gel and then transferred to nitrocellulose sheets. The transferred proteins were then reacted with supernatants from hybridoma tissue cultures denominated S10F03 (lane 1) or S22C06 (lane 2) or an anti-influenza hemagglutinin hybridoma used as a negative control. This procedure of polyacrylamide gel separation follwed by transfer to nitrocellulose and visualization is referred to hereinafter as a Western blot procedure. Protein visualization was accomplised as described in the Materials and Methods section, hereinafter.

FIG. 1 illustrates the immunological detection of the p85 oncoprotein ligand by the monoclonal receptors secreted by hybridomas S10F03 (ATCC HB 8596) and S22C06 (ATCC HB 8595), using an external standard for the p85 oncoprotein ligand and an influenza hemagglutinin-recognizing Mab as a negative control. FIG. 2 illustrates similar results again using Mabs from hybridoma S10F03 as well as Mabs from hybridomas P43D09 (ATCC HB 8594), and P44E11 (ATCC HB 8593), and also hybridoma P42C10. A monoclonal antibody against the Rouscher virus protein denominated gp70 [Niman and Elder in *Monoclonal Antibodies and T Cell Products,* above] was used as a negative control.

FIG. 3 further illustrates the specificity of the monoclonal receptors of this invention. There, CCL64 mink cells (lanes B and D) or MSTF cells infected with FeLV-B and FeSV (lanes A and B) were radioactively labeled with $^{32}P$. Extracts from the labeled cells were then incubated with either a goat antiserum against the p15 protein encoded by the gag portion of the v-fes gene and expressed as the protein precursor denominated pr65 (lanes A and B) or with tissue culture supernatant from hybridoma S10F03 (lanes C and D).

As can be seen, the Mab of this invention from hybridoma S10F03 bound only to the p85 oncoprotein ligand (lane C), while the goat anti-p15 serum bound to both the pr65 and p85 fusion oncoproteins from the infected cells (lane A). No proteins were bound from the uninfected cells (lanes B and D). These results and, by analogy, discussion of the assay concerning FIG. 13, confirm that the Mabs of this invention bind only to the oncoprotein ligand (p85) a portion of whose amino acid residue sequence corresponds to the sequence of the immunogenic polypeptide used to prepare the hybridoma secreting each Mab.

In similar results, not shown, Mabs from the above five hybridomas also bound to the 108K dalton oncoprotein ligand expressed in cells transformed by GA-FeSV. The oncoprotein ligand encoded by the GA-FeSV strain is substantially identical in amino acid residue sequence to the oncoprotein ligand encoded by the ST-FeSV strain in the region of the immunogenically useful polypeptide. See, Hampe et al., *Cell,* 30, 777–785 (1982).

None of the above five Mabs bound to the oncoprotein encoded by the v-fps gene of the Fujinami strain of avian sarcoma virus. The predicted v-fps oncoprotein also contains extensive homologies to the predicted v-fes oncoprotein and differs in the region corresponding to the above 12-mer (polypeptide b) only by the substitution of the first and fourth residues from the amino-terminus of that 12-mer polypeptide; i.e., the amino-terminal serine (S) of the v-fes-related polypeptide and oncoprotein is replaced by a valine (V) in the v-fps-related oncoprotein, and the second proline (P) residue from the amino-terminus is replaced by an alanine (A) residue.

The non-binding of the above Mabs to the v-fps-related oncoprotein provides a basis for distinguishing among expressed oncoproteins in transformed cells, and for assaying for the presence of the v-fes-related oncoprotein ligand in the presence of the v-fps-related oncoprotein. That distinction in binding can also be useful in purifying a mixture of both proteins by affinity chromatography utilizing an Mab of this invention as a portion of an affinity sorbant, as is discussed hereinafter.

The above non-binding of the monoclonal antibodies of this invention to the v-fps-related oncoprotein also highlights the improvement in specificity of the monoclonal receptors over previously obtained oligoclonal receptors. Thus, Sen et al., *Proc. Natl. Acad. Sci. USA*, 80, 1246–1250 (1983), used polypeptide (b) above conjugated to KLH to prepare rabbit oligoclonal antibodies. Those oligoconal antibodies bound to oncoproteins expressed in cells transformed by ST-FeSV, GA-FeSV and FSV (Fuginami sarcoma virus) that contain the v-fes$^{ST}$, v-fes$^{GA}$ and v-fps oncogenes, respectively. It can therefore be seen that the specificity obtained from the monoclonal receptors of this invention is greatly improved over that obtained with oligoclonal receptors even when both are raised to the same immunogenic polypeptide.

In a similar manner are prepared hybridomas that secrete monoclonal receptors that bind to oncoprotein molecule ligands, e.g., PDGF, to immunogenic polypeptides encoded by the retroviral oncogenes denominated fes, myb, sis, ras, myc and mos, as well as to immunogenic polypeptides whose sequences correspond to sequences of oncoproteins encoded by oncogenes denominated fps, src, yes, fqr, fms, erb-B, mht, raf, abl and rel, and also to oncoproteins expressed in cells transformed by retroviruses containing those genes. Specific monoclonal receptors of this invention bind to an immunogenic polypeptide encoded by the above oncogenes.

Some of those oncogenes are named below and are illustrated adjacent to formulae of the polypeptides encoded by those sequences to which the preferred monoclonal receptors of this invention bind. The right-hand column illustrates those instances where oligoclonal antisera raised to an enumerated polypeptide have been shown to contain antibodies (receptors) that bind to the oncoprotein that contains an amino acid residue sequence corresponding to the sequence of the polypeptide using a Western blot analysis. Binding is shown by a plus sign (+), and oligoclonal receptor-containing antisera for which a plus sign is listed exhibited a 50 percent binding titer as described before. The designation "NT" indicates that a rigorous binding study has not been conducted. The polypeptide formulae contain the amino acid residue sequences shown, illustrated from left to right and in the direction from amino-terminus to carboxy-terminus.

| Oncogene | Polypeptide Sequence | Binding of Oligoclonal Antisera to Oncoproteins |
|---|---|---|
| fes | SDVWSFGILLWETFSLGASPYPNLSNQQTR; | + |
|  | SPYPNLSNQQTR; | + |
|  | IHRDLAARNCLVTEKN; | NT |
|  | IGRGNFGEVFSG; | + |
|  | LMEQCWAYEPGQRPSF; | + |
|  | VPVKWTAPEALNYGR; and | + |
|  | SSGSDVWSFGILLWE; | NT |
| myb | RRKVEQEGYPQESSKAG; and | + |
|  | RHYTDEDPEKEKRIKELEL; | + |
| sis | RKIEIVRKKPIFKKATV; and | + |
|  | RVTIRTVRVRRPPKGKHRKC; | + |
| ras | YREQIKRVKDSDDVPMVLVGNKC; | + |
|  | KLVVVGARGVGK; | + |
|  | KLVVVGASGVGK; | + |
|  | KLVVVGAVGVGK; and | NT |
|  | KLVVVGAGGVGK; | + |
| myc | CDEEENFYQQQQQSEL; | + |
|  | PAPSEDIWKKFEL; | + |
|  | LPTPPLSPSRRSGLC; | + |
|  | CDPDDETFIKNIIIQDC; | NT |
|  | CSTSSLYLQDLSAAASEC; | + |
|  | CASQDSSAFSPSSDSLLSSTESSP; and | NT |
|  | CTSPRSSDTEENVKRRT; | + |
| mos | LPRELSPSVDSR; | + |
|  | RQASPPHIGGTY; and | + |
|  | TTREVPYSGEPQ; | + |
| erb-B | ENDTLVRKYADANAVCQ | NT |
|  | LGSGAFGTIYKG(C) | NT |
|  | IMVKCWMIDADSRPKF | NT |
| PDGF-2* | SLGSLTIAEPAMIAECK; | + |
|  | RKIEIVRKKPIFKKATV; and | + |
|  | RVTIRTVRVRRPPKGKHRKC; | + |
| PDGF-1* | SIEEAVPAECKTR | + |

The polypeptides useful for inducing the production of oligoclonal receptors, and ultimately for production of monoclonal receptors, are preferably linked to a carrier molecule, as discussed herein wherein polypeptides linked to KLH have been utilized throughout as illustrative polypeptide-carrier conjugates. For polypeptides that contain fewer than about 35 amino acid residues, it is preferable to use a carrier for the purpose of inducing the production of oligoclonal and monoclonal receptors. Polypeptides containing about 35 to about 40 amino acid residues may be used alone, without linkage to a carrier, to induce receptor production, although it is still preferable to utilize a carrier for producing those receptors. Thus, the receptors may be induced by or raised to a polypeptide alone, or linked to a carrier.

B. Immunization Binding Studies

As noted several times, the polypeptides utilized in raising oligoclonal antibodies and hybridomas that secrete monoclonal antibodies are themselves immunogenic and antigenic, and those properties provide criteria for identifying useful polypeptides for hybridoma preparation. The discussion below relates to studies with oligoclonal antibody (receptor)-containing antisera induced by or raised to polypeptides used in the preparation of hybridomas that secrete monoclonal receptors (antibodies) to oncoproteins encoded by the ras, sis, erb-B and myb oncogenes. As will be described, the sis-related polypeptide induces production of oligoclonal receptors that bind not only to the polypeptide, but also to a corresponding oncoprotein, human platelet-derived growth factor (PDGF). The oligoclonal antibodies so prepared exhibited the before-described 50 percent binding titer to the immunizing polypeptide, thereby indicating that monoclonal antibodies (receptors) of this invention may also be prepared by fusion of the antibody-producing splenocytes with cells of a suitable myeloma line.

PDGF isolated from platelets consists of two chains that are approximately sixty percent homologous at the amino-terminal end. One of those chains (PDGF-2) is virtually identical to a portion of the simian sarcoma virus (v-sis) gene product (p28$^{sis}$). Sequencing of the human c-sis and v-sis terminate at the same position and the PDGF-2 molecule originates from a larger precursor which has extensive homology with p28$^{sis}$. The homology between p28$^{sis}$ and PDGF-2 begins at amino acid residue 67 of p28$^{sis}$ and the amino-terminus of PDGF-2, and has recently been extended to the predicted carboxy-terminus of p28$^{sis}$ via the isolation and sequencing of a human c-sis clone. Josephs et al., *Science*, 223, 487–491 (1984).

p28$^{sis}$ is rapidly cleaved to generate p20$^{sis}$ which presumably has the same amino terminus as PDGF-2. Within the region coding for p20$^{sis}$ and PDGF-2 there are eight amino acid changes that can be placed into three regions. The two changes near the amino terminus are conservative, five changes are clustered near the center of the molecule, and one change is located in the carboxyl-terminal portion.

Two exemplary polypeptides were prepared. The first, denominated polypeptide (c), corresponds in amino acid residue sequence to residues 139 through 155 of the predicted sequence of the simian sarcoma virus transforming protein denominated p28$^{sis}$. Devare et al., *Proc. Natl. Acad. Sci. USA*, 80, 731–735 (1983). The sequence of polypeptide (c) also corresponds to the sequence of positions 73 through 89 from the amino-terminus of the protein chain denominated PDGF-2 of human platelet-derived growth factor, as noted before. The second, denominated polypeptide (d), corresponds in amino acid residue sequence to residues 2 through 18 of the predicted sequence of the transforming protein of the avian myeloblastosis virus (v-myb) oncoprotein. Rushlow et al., *Science*, 216, 1421–1423 (1982). The amino acid residue sequence of polypeptides (c) and (d) are shown below, from left to right and in the direction from amino-terminus to carboxy-terminus:

| polypeptide (c) | RKIEIVRKKPIFKKATV; |
| polypeptide (d) | RRKVEQEGYPQESSKAG. |

Each of the polypeptides was synthesized and bound to KLH using a Cys residue of their carboxy-terminii (not shown in the above formulas), and each resulting conjugate was then used to immunize mice as discussed generally in the Materials and Methods section. As can be seen from an examination of FIG. 4, sera raised to polypeptide (c) contained oligoclonal receptors that bind to polypeptide (c) as well as to KLH, and sera raised to polypeptide (d) contained oligoclonal receptors that bind to polypeptide (d) and to KLH. Neither serum contained receptors that cross-react and bind to the polypeptide not used to raise them.

Extracts from outdated human platelets were used to obtain partially purified samples of PDGF. As already noted, PDGF is an oncoprotein having an apparent molecular weight of about 30K daltons that can be reductively cleaved into two high molecular weight polypeptides of similar apparent molecular weights, and designated PDGF-1 and -2.

FIG. 5 shows the results of Western blot analysis of PDGF using the oligoclonal receptor-containing antisera raised to polypeptides (c) and (d), as is discussed in more detail in the description of that figure; the antiserum raised to polypeptide (d) being used as a negative control. As can be seen from an examination of FIG. 5; the oligoclonal receptor-containing serum raised to the sis-related polypeptide, polypeptide (c), bound to three proteinacious moieities (lane 2). One of those moieties has an apparent molecular weight of about 30K daltons and two of about 16-18K daltons each. Lane 4 also illustrates binding by oligoclonal receptors contained in the anti-sis-related polypeptide serum. As expected, only non-specific binding was shown by oligoclonal receptors raised to the myb-related polypeptide, polypeptide (d), (lanes and 5).

Presuming that the amino acid residue sequence of PDGF—1 and —2 are colinear with the sequence of p28$^{sis}$, the amino acid residue sequence of the polypeptide (c) corresponds to positions 67 through 83, and 73 through 89 of PDGF—1 and —2, respectively. The amino acid residue sequence of residues 73 through 80 of PDGF 2 has been determined [Doolittle et al., *Science*, 221, 275–277 (1983)] and all of the those residues are identical to the first (amino-terminal) eight residues of polypeptide (c). In addition, a polypeptide from PDGF and corresponding to residues 147 through 155 of the p28$^{sis}$ oncoprotein has been sequenced [Waterfield, *Nature*, 304, 35–39 (1983)], and of the nine residues so far identified, all are identical to the corresponding residues of polypeptide (c). Thus, sixteen of the seventeen residues of polypeptide (c) are identical to and in the same sequence as residues in both PDGF, derived from humans, and p28$^{sis}$ derived from a line of retrovirus-transformed cells.

The above results thus illustrate the immunogenicity and antigenicity of two additional polypeptides useful for immunizations leading to the preparation of hybridomas that secrete monoclonal receptors of this invention. Those results also show that the oligoclonal receptors raised to polypeptide (c) also bind to an oncoprotein; i.e., PDGF, PDGF-1 and PDGF-2.

Additional synthetic polypeptides representing various regions of both PDGF sequences were made. The amino terminii of PDGF-1 and PDGF-2, as well as the central and carboxy-terminal portion of PDGF-2 were synthesized, conjugated to the immunogenic carrier keyhole limpet hemocyanin (KLH), and injected into mice to induce production of oligoclonal receptor-containing antisera that exhibited the before-described 50 percent binding titer.

The polypeptide representing the unique region of PDGF-2 contains the first 17 amino acids of this sequence and will be called PDGF-2(1–17), wherein the parenthesized numerals indicate the amino acid residues of the corresponding molecule numbered from aminoterminus. The unique region of PDGF-1 is represented by a polypeptide PDGF-1(1–12), that contains the first 12 amino acids of that sequence. Six of those 12 amino acids are shared with PDGF-2 but only three are consecutive, as noted before. The third polypeptide, PDGF-2(73–89) is also referred to herein as polypeptide (c). It represents the predicted amino acid residues 139–155 of $p28^{sis}$ and contains an additional cysteine at its carboxy-terminus for coupling purposes. This polypeptide when coupled to KLH induced production of antibodies that recognize the reduced subunits of purified PDGF, proteins of Mr 31,000, 30,000, 21,000 and 18,000–14,000 in a platelet extract, and a 56K dalton protein in SSV-infected marmoset cells. The fourth polypeptide, PDGF-2(126–145), was also predicted by the v-sis sequence (residues 192–211 of $p28^{sis}$). Amino acid sequences of these polypeptides have been illustrated hereinbefore.

To analyze the specificity of the oligoclonal receptor-containing antisera generated against these synthetic polypeptide conjugates, PDGF was probed with these antisera. Purified PDGF was reduced and electrophoresed into a polyacrylamide gel, and then onto nitrocellulose (FIG. 6, lanes A–F) using a Western blot procedure. In lanes A and B, two antisera directed against PDGF-1(1–12) immunoreacted with a protein of approximately 18,000 daltons. Sequence analysis of purified PDGF indicates the majority of the PDGF-1 chain migrates at this position [Antonaides, et al., Science, 220, 963–965 (1983)]. The weakness of the reactivity with these antisera suggests the amino-terminal end of PDGF-1 may not be readily accessible for antibody binding.

In contrast, antiserum against the amino-terminus of PDGF-2(1–17) (lane C) readily detected a protein migrating at about 18,000 and 14,000 daltons, consistent with sequence analysis of PDGF-2 (Antonaides et al., supra.).

The antisera induced by PDGF-2(73–89) produced the same activities (lanes D,E) as seen in lane C. In contrast, antisera against PDGF-2(126–145) did not have detectable activity against purified PDGF.

Since the sequence of the PDGF-2(126–145) polypeptide differs from c-PDGF at position 145 (Josephs, et al., supra), it is possible that this amino acid residue change is contained within the epitopic site. This is unlikely because the polypeptide is 20 amino acid residues long and the change is only on the carboxy-terminal position that is used to couple the polypeptide to the KLH carrier protein. The lack of activity is thus not due to generation of oncopolypeptide-specific antibodies because this antiserum reacts with cell-derived PDGF-like molecules. The 14,000 to 18,000 dalton size of the detected PDGF in purified preparations suggests that most of this material is missing the carboxy-terminal end of the predicted sequence of $p28^{sis}$, which would remove all or part of the PDGF antigenic site recognized by this antiserum.

In order to determine if PDGF-like proteins might also be synthesized in other transformed cell lines, extracts were made and were immunoreacted with various oligoclonal receptor-containing antisera against PDGF-related polypeptides. In FIG. 7, the SSV-transformed NIH 3T3 cells were probed with an oligoclonal receptor-containing antiserum induced by PDGF-1(1–12) (lanes A-C, F-H and K-M) and by PDGF-2(73–89) (lanes D,E,I.J,N and O). Of the two sera against PDGF-2(73–89) (FIG. 6, lanes D and E), the serum used in FIG. 6, lane D produced a somewhat weaker activity with purified PDGF. However, as seen in lane D of FIG. 7, a strong reactivity with a protein of approximately 70,000 daltons was observed that was blocked by preincubation with the immunizing polypeptide, PDGF-2(73–89)(lane E), but was not blocked by preincubation of the antiserum with PDGF-1(1–12).

Similarly, in FIG. 13, a protein related to the ras oncogene is detected by a monoclonal antibody (ATCC HB 8679) to a ras synthetic peptide. The protein is detected in Lane A and blocked by preincubation with the immunizing peptide (Lane B). Thus, the preincubation with the immunizing polypeptide blocked the strongly reactive oncoprotein.

Thus, the specific reactivity with these oncoproteins by both antisera demonstrates that this is not a fortuitous cross-reactivity with a small region of PDGF, but that this molecule contains sequences homologous to at least the amino-terminus of PDGF-1 and the central region of PDGF-2. The amounts of $p28^{sis}$ and $p20^{sis}$ were below the level of detection with this anti-PDGF-2(73–89) serum. Similar results were obtained with additional antisera, although overexposure did occasionally show a 20,000 dalton band was specifically detected (data not shown).

Analysis of extracts of two other unrelated transformed cells with these antisera gave similar results. The TRD1 cell line is a spontaneously transformed Balb/3T3 cell line [Bowen-Pope et al., Proc Natl. Acad. Sci. U.S.A., 81, 2396–2400 (1984)]. This line also expresses a 70,000 dalton protein as well as a more immunologically related protein of approximately 100,000 daltons (FIG. 7, lanes G–I). A third cell line, MSTF, and a mink lung line (CCL64) productively infected with FeLV-B and the Synder-Theilen strain of FeSV, also expresses the same size protein FIG. 7, lanes K-O.

In addition to the 70,000 dalton oncoprotein, an oligoclonal receptor-containing antiserum against PDGF-1(1–12) detected proteins of approximately 53,000 daltons (data not shown). These proteins are not serum contaminants because they are detected in extracts of cells that have been grown for one month in the absence of serum and are found in serum free media conditioned by the TRD1 cell lines. All cell lines studied contain these two PDGF-like proteins, (See also discussion of FIG. 11 in "Brief Description of Figures").

The expression of PDGF-like molecules in a broad spectrum of cells, including cells that are not oncogenically transformed (normal diploid rat smooth muscle and human lung fibroblasts), indicates that other processes are involved in transformation. Although all of the cell lines contained 70,000 and 53,000 dalton proteins detected with oligoclonal receptor-containing antisera induced by PDGF-1(1–12), the cells were quite heterogeneous with regard to size and intensity of other proteins detected with antisera directed against determinants predicted by the sequence of the PDGF-2 region (data not shown). The nature of these differences is presently unknown.

In a similar manner, each of the four immunogenic polypeptides, denominated (e-h) below, may be used to induce oligoclonal receptors that bind to those immunogenic polypeptides used to induce their production as well as to each of two oncoproteins encoded by the ras oncogene. The sequences of those four ras-related polypeptides, in the direction from left to right and from amino-terminus to carboxy-terminus, are represented by the formulas:

| polypeptide e | KLVVVGARGVGK; |
|---|---|
| polypeptide f | KLVVVGASGVGK; |
| polypeptide g | KLVVVGAVGVGK; |
| polypeptide h | KLVVVGAGGVGK; or | by the combined formula:

polypeptide (e-h)

KLVVVGAR(S,V,G)GVGK;

wherein the amino acid residues in parentheses are each an alternative to the immediately preceding amino acid residue in the formula. The oligoclonal receptors so prepared have a 50 percent binding titer dilution of more than 1:400 after two immunizations, as described before, in about a one month period. Additionally, each ras-related oligoclonal receptor induced by polypeptides (e), (f) and (h) have been shown to bind to an oncoprotein present in lysed cell extracts from (a) human T24 bladder carcinoma cells and also (b) Harvey murine sarcoma virus-infected mouse 3T3 cells (data not shown).

As is seen in FIG. 12, each of the two immunogenic polypeptides denominated below (k and l) may be used to induce oligoclonal receptors that bind to those immunogenic polypeptides used to induce their production as well as to each of two oncoproteins encoded by the v-fes$^{ST}$ oncogene. The sequence of the two v-fes-related polypeptides, in the direction from left to right and from amino-terminus to carboxy-terminus are represented by the formulae:

| polypeptide k | LMEQCWAYEPGQRPSF |
|---|---|
| polypeptide l | IGRGNFGEVFSG. |

The oligoclonal receptors induced by polypeptides (k) and (1) have been shown to bind to an oncoprotein present in supernatant from cells of human T24 bladder carcinoma and a spontaneously transformed mouse 3T3 cell line (Lanes A and C).

The use of monoclonal receptors of this invention such as those raised to the sis-(PDGF)related polypeptide (c), or to the fes-related polypeptides (a), (b) (k) or (l), or to the ras-related polypeptides (e-h) or to the other oncoprotein-related polypeptides disclosed herein in the affinity sorbants described below provides a convenient and less arduous means for preparing naturally occurring proteinaceous materials that are otherwise difficult to obtain in purified form such as PDGF. Thus, rather than having to go through the long procedure to obtain purified PDGF, discussed hereinafter, one may, for example, merely lyse the cells, centrifuge, pour the supernatant through an affinity sorbant column containing bound anti-polypeptide (c) receptor, and elute the purified protein after dissociating the formed, reversible ligand complex. While some additional proteinaceous material may be non-specifically bound to the affinity sorbant column, the isolation of purified proteins that are otherwise difficult to obtain in such form is greatly enhanced using such sorbants.

III. DIAGNOSTIC SYSTEMS AND METHODS

A diagnostic system, preferably in kit form, comprises yet another embodiment of this invention. This system is useful for assaying for the presence of an oncoprotein ligand by the formation of an immune reaction. This system includes at least one package that contains biologically active monoclonal receptor molecules of this invention. Thus, the receptor binds to (a) a polypeptide containing about 7 to about 40, and preferably about 10 to about 30, amino acid residues in an amino acid residue sequence that corresponds to a portion of the amino acid residue sequence of an oncoprotein ligand encoded by a gene of a retrovirus, and (b) the oncoprotein ligand encoded by the retroviral gene. When a predetermined amount of moncolonal receptor molecules is admixed with a predetermined amount of an aqueous composition containing an oncoprotein ligand, an immunological reaction occurs that forms a complex between the receptor and the ligand. Exemplary aqueous compositions containing an oncoprotein include, without limitation, cell lysates, serum, plasma, urine and amniotic fluid. It is a particularly novel aspect of this invention to assay urine in accordance with the methods set forth herein.

Admixture between receptor and ligand occurs in an aqueous composition. However, either the receptor or ligand may be substantially dry and water-free prior to that admixture. Thus, a solution of the receptor in hybridoma supernatant, ascites fluid or buffer may be admixed with an aqueous cell extract to admix the reagents from two aqeuous compositions; the receptor may be coated on the walls of a microtiter plate and then admixed with a cell extract or serum containing the ligand; or the ligand may be coated on microtiter plate walls, on a nitrocellulose sheet in an acrylamide gel or the like, or may be present in a tissue section, and hybridoma supernatant, ascites fluid or a buffer solution containing the receptor admixed therewith.

The use of exemplary diagnostic systems and methods of this invention is illustrated in the discussions of FIGS. 1-3 and 10. There, oncoprotein ligands coated onto nitrocellulose and then admixed with a receptor of this invention are discussed in relation to FIGS. 1, 2, 10 and 13, while a cell extract incubated with hybridoma supernatant to form an immunological complex is discussed regarding FIGS. 3 and 13.

Receptors are utilized along with an "indicating group" or a "label". The indicating group or label is utilized in conjunction with the receptor as a means for determining whether an immune reaction has taken place and an immunological complex has formed, and in some instances for determining the extent of such a reaction.

The indicating group may be a single atom as in the case of radioactive elements such as iodine 125 or 131, hydrogen 3, or sulfur 35, or carbon 14, or NMR-active elements such as fluorine 19 or nitrogen 15. The indicating group may also be a molecule such as a fluorescent dye like fluoresein, rhodamine B, or an enzyme, like horseradish peroxidase (HRP) or glucose oxidase, or the like.

The indicating group may be bonded to the receptor as where an antibody is labeled with $^{125}$I. The indicating group may also constitute all or a portion of a separate molecule or atom that reacts with the receptor molecule such as HRP-linked to rabbit anti-mouse antibodies where the antibody receptor was raised in a mouse, or where a radioactive element such as $^{125}$I is bonded to protein A obtained from *Staphylococcus aureus*.

Where the principal indicating group is an enzyme such as HRP or glucose oxidase, additional reagents are required to visualize the fact that an immune reaction has occurred and the receptor-ligand complex has formed. Such additional reagents for HRP include hydrogen peroxide and an oxidation dye precursor such as diaminobenzidine. Additional reagents useful with glucose oxidase include ABTS dye, glucose and HRP.

The terms "indicating group" or "label" are used herein to include single atoms and molecules that are linked to the receptor or used separately, and whether those atoms or molecules are used alone or in conjunction with additional reagents. Such indicating groups or labels are themselves well-known in immunochemistry and constitute a part of this invention only insofar as they are utilized with otherwise novel receptors, methods and/or systems.

An indicating group or label is preferably supplied along with the receptor and may be packaged therewith or packaged separately. Additional reagents such as hydrogen peroxide and diaminobenzideine may also be included in the system when an indicating group such as HRP is utilized. Such materials are readily available in commerce, as are many indicating groups, and need not be supplied along with the diagnostic system. In addition, some reagents such as hydrogen peroxide decompose on standing, or are otherwise short-lived like some radioactive elements, and are better supplied by the end-user.

The diagnostic system may also include a solid matrix that may be 96 well microtiter plates sold under the designation Immulon II (Dynatech, Alexandria, VA). The microtiter strip or plate is made of a clear plastic material, preferably polyvinyl chloride or polystyrene. Alternative solid matrices for use in the diagnostic system and method of this invention include polysyrene beads, about 1 micron to about 5 millimeters in diameter, available from Abbott Laboratories, North Chicago, IL; polystyrene tubes, sticks or paddles of any convenient size; and polystyrene latex whose polystrene particles are of a size of about 1 micron and can be centrifugally separated from the latex.

The solid matrix may also be made of a variety of materials such as cross-linked dextran, e.g., Sephadex G—25, —50, —100, —200, and the like available from Pharmacia Fine Chemicals of Piscataway, NJ, agarose and cross-linked agarose, e.9., Sepharose-6B, CL-6B, 4B, CL46 and the like, also available from Pharmacia Fine Chemicals.

The diagnostic system may further include a standard against which to compare the assay results and various buffers in dry or liquid form for, inter alia, washing microtiter plate walls, diluting the sample, diluting the labeled reagent, or the like.

An ELISA assay is another contemplated embodiment of this invention. Here, an aqueous composition to be assayed for the presence of an oncoprotein ligand, such as concentrated urine is bound or otherwise affixed to a solid matrix such as a microtiter test well to form a solid support. A liquid solution such as phosphate-buffered saline, hybridoma supernatant or ascites fluid containing a monoclonal receptor of this invention is admixed with the solid support to form a solid-liquid phase admixture. The solid-liquid phase admixture is maintained for a time period sufficient for the monoclonal receptor to bind to (immunoreact with) oncoprotein ligand of the solid support, i.e., affixed to the solid matrix. The solid and liquid phases are thereafter separated, and the amount of monoclonal receptor bound to the solid support and thereby the amount of oncoprotein ligand in the assayed sample are determined. Such determinations are typically carried out using a radioisotope- or enzyme-labeled antibody or *Staphylococcus aureus* protein A that binds specifically to a monoclonal receptor of this invention.

IV. AFFINITY SORBANTS

Affinity sorbants in which the monoclonal receptor molecules of this invention constitute the active, binding portions constitute yet another embodiment of this invention.

In this embodiment, the monoclonal receptor molecules of this invention are linked to a solid support that is chemically inert to the oncoprotein ligands to be purified by those sorbants. The phrase "chemically inert" is used herein to mean that a chemical reaction between the solid support and the oncoprotein ligands does not occur. However, physical interactions between the solid support and the oncoprotein ligands such as non-specific binding can and do occur between them, although such interactions are preferably minimized.

The solid support may be made of a variety of materials such as cross-linked dextran, e.g., Sephadex G—25, —50, —100, —200 and the like available from Pharmacia Fine Chemicals of Piscataway, New Jersey, agarose and cross-linked agarose, e.g., Sepharose 6B, CL6B, 4B, CL4B and the like also available from Pharmacia Fine Chemicals or Bio-Gel A-0.5M, A-1.5M, A-50M and the like available from Bio-Rad Laboratories, Richmond California, or polyacrylamide beads, e.g., Bio-Gel P-2, P-30, P-100, P-300 and the like also available from Bio-Rad Laboratories. Polyacrylamide beads have the lowest tendency for non-specific binding among the above supports, but also typically have a low porosity that limits their binding capacity. The agarose and cross-linked agarose materials are preferred herein and will be used illustratively as a solid support.

The agarose support is typically activated for linking using cyanogen bromide. The activated support is then washed and linked to the receptor molecules without drying of the activated support. The support-linked receptor is then washed and is ready for use. Unreacted reactive groups on the support can be reacted with an amine such as ethanolamine or Tris, if desired, although those reactive groups decay quickly.

The affinity sorbant may be used in its loose state, as in a beaker or flask, or it may be confined in a column. Prior to use, it is preferable that the affinity sorbant be washed in the buffer or other aqueous medium utilized for oncoprotein purification to eliminate non-specifically bound proteins or those receptors that were unstably linked to the support.

An aqueous composition containing an oncoprotein ligand having an amino acid residue sequence corresponding to the amino acid residue sequence of the polypeptide to which the linked receptor of the affinity sorbant binds such as serum or a cell extract is provided, and then admixed with the affinity sorbant. That admixture forms a reversible, linked receptor-ligand complex between the linked receptor and the oncoprotein ligand.

The ligand receptor-ligand complex is then separated from the remainder of the un-complexed aqueous composition to thereby obtain the oncoprotein in purified form linked to the affinity sorbant. When the admixture takes place in a beaker or flask, this separation can be made by filtration and washing. When the sorbant is in a column, the separation may take place by elution of the un-complexed aqueous medium, again, preferably, follwed by a washing step.

When the purified protein is desired free from the affinity sorbant, it can typically be obtained by a variety of procedures. In any of those procedures, the reversible linked receptor-ligand complex is dissociated into its component parts of support-linked receptor and oncoprotein ligand, followed by separating that ligand from the linked-receptor to provide the purified oncoprotein free from the affinity sorbant.

The dissociation of the reversible complex may be effected in a number of ways. A 0.2 molar glycine hydrochloride solution at a pH value of about 2.5 is typically utilized. Alternatively, the bound ligand can be competed away from the linked receptor by admixture of the reversible complex with an excess of the immunogenic polypeptide utilized to raise the receptor. Such a competition avoids possible denaturation of the ligand. Separation of the dissociated oncoprotein ligand from the affinity sorbant may be obtained as above.

The preparation of affinity sorbants and their use is broadly old. However, such materials and uses that incorporate the receptor molecules of this invention have not been heretofore available. A detailed description of affinity sorbants, their methods of preparation and use wherein the antigen is linked to the support may be found in *Antibody as a Tool*, Marchalonis and Warr eds., John Wiley & Sons, New York, pages 64-67 and 76-96 (1982).

V. MATERIALS AND METHODS

A. Growing Of Viruses And Cell Lines

An uninfected mink lung cell line (CCL64), the same line productively transformed with the Snyder-Theilen strain of feline sarcoma virus (ST-FeSV) and feline leukemia virus B (FeLV-B) and designated MSTF, as well as the same line non-productively infected with Gardner-Arnstein feline sarcoma virus (GA-FeSV) and designated 64F3C17 were cultured as described in Sen et al., *Proc. Natl. Acad. Sci. USA*, 80, 1246-1250 (1983). A non-producing avian myeloblast cell line, non-productively infected with avian myeloblastosis virus was cultured as described in Duesberg et al., *Proc. Natl. Acad. Sci. USA*, 77, 5120-5124 (1980). The non-producing marmoset cell line, non-productively infected with simian sarcoma virus (SSV) and designated NPV/SiSV and NPVI/SiSV were cultured as described in Devare et al., *Proc. Natl. Acad. Sci. USA*, 80, 731-735 (1983). The avian fibroblast non-productively transformed cell line infected with Fujinami sarcoma virus (FSV) was a gift from B. Sefton of the Salk Institute, La Jolla, California. Uninfected mouse NIH 3T3 fibroblast cells and mouse NIH 3T3 fibroblast cells productively infected with Harvey murine sarcoma virus were cultured as described in Todaro et al., *J. Cell Biol.*, 17, 299-313 (1963); and Harvey, *Nature*, 204, 1104-1105 (1964).

Human T24 bladder carcinoma cells were cultured as described in Bubenik et al., *Int. J. Cancer*, 11, 765-773 (1973).

B. Synthesis of Peptides

Polypeptides were synthesized using solid phase methods as described in Marglin and Merrifield, *A. Rev. Biochem.*, 39, 841-866 (1970), and were confirmed by amino acid analyses. Sequence information is derived from either amino acid sequencing of the viral protein or predictions based upon nucleotide sequencing. The sources of the sequence information were as listed in the footnotes relating to those sequences and their oncogenes.

For polypeptides having fewer than 35 residues that were used in immunizing inocula, a cysteine residue was added to the amino-terminus or to the carboxyl-terminus of each polypeptide whose corresponding oncoprotein sequence did not contain such a residue. The Cys residues were used to assist in coupling to a protein carrier as described below.

In preparing a useful synthetic polypeptide by the above solid phase method, the amino acid residues were linked to a cross-linked resin (solid phase) through an ester linkage from the carboxy-terminal residue. When the polypeptide was linked to a carrier via a Cys residue, that Cys residue was conveniently used as the carboxy-terminal residue that was ester-bonded to the resin.

The alpha-amino group of each added amino acid was typically protected by a tertiary-butoxycarbonyl (t-BOC) group prior to the amino acid being added into the growing polypeptide chain. The t-BOC group was then removed by standard techniques prior to addition of the next amino acid to the growing polypeptide chain.

Reactive amino acid side chains were also protected during synthesis of the polypeptides. Usual side-chain protecting groups were used for the remaining amino acid residues as follows: O-(p-bromobenzyloxycarbonyl) for tyrosine; O-benzyl for threonine, serine, aspartic acid and glutamic acid; S-methoxybenzyl for cysteine, dinitrophenyl for histidine; 2-chlorobenzoxycarbonyl for lysine and tosyl for arginine.

Protected amino acids were recrystallized from appropriate solvents to give single spots by thin layer chromatography. Couplings were typically carried out using a ten-fold molar excess of both protected amino acid and dicyclohexyl carbodiimide over the number of milliequivalents of initial N-terminal amino acid. A two molar excess of both reagents may also be used. For asparagine, an equal molar amount of N-hydroxy-benzotriazole was added to the protected amino acid and dimethyl formamide was used as the solvent. All coupling reactions were more than 99% complete by the picric acid test of Gisin, *Anal. Chem. Acta.* 58:248-249 (1972).

After preparation of a desired polypeptide, a portion of the resulting, protected polypeptide (about 1 gram) was treated with two milliliters of anisole, and anhydrous hydrogen flouride, about 20 milliliters, was condensed into the reaction vessel at dry ice temperature. The resulting mixture was stirred at about 4 degrees C. for about one hour to cleave the protecting groups and to remove the polypeptide from the resin. After evaporating the hydrogen flouride at a temperature of 4 degrees C. with a stream of $N_2$, the residue was extracted with anhydrous diethyl ether three times to remove the anisole, and the residue was dried in vacuo.

The vacuum dried material was extracted with 5% aqueous acetic acid (3 times 50 milliliters) to separate the free polypeptide from the resin. The extract-containing solution was lyophilized to provide an unoxidized, synthetic polypeptide.

C. Coupling of Synthetic Polypeptides To Carrier Protein

The unoxidized synthetic polypeptides were coupled to the carrier protein keyhole limpet hemocyanin (KLH) through a cysteine residue (Cys; C) of the polypeptide with m-maleimdobenzoyl-N-hydroxysuccinimide ester as the coupling reagent as described in Green et al., *Cell*, 28, 477 and 487 (1982). Where a Cys residue was a terminal residue in a sequence, an additional cysteine residue was not added.

Briefly, as a generalized procedure for each polypeptide, 4 milligrams of KLH in 0.25 millileters of 10 millimolar sodium phosphate buffer (pH 7.2) were reacted with 0.7 milligrams of MBS that was dissolved in dimethyl fermamide (DMF), and the resulting admixture was stirred for 30 minutes at room temperature. The MBS solution was added dropwise to ensure that the local concentration of DMF was not too high, as KLH is insoluble at DMF concentrations of about 30% or higher. The reaction product, KLH-MB, was passed through a chromatography column prepared with Sephadex G-25 (Pharmacia Fine Chemicals, Piscataway, NJ) equilibrated with 50 millimolar sodium phosphate buffer (pH 6.0) to remove free MBS. KLH recovery from peak fractions of the column eluate, monitored at 280 nanometers, was estimated to be approximately 80%.

The KLH-MB so prepared was then reacted with 5 milligrams of polypeptide dissolved in 1 milliliter of buffer. The pH value of the resulting reaction composition was adjusted to 7-7.5, and the reaction composition was stirred at room temperature for 3 hours.

D. Immunization And Fusion

1. fes-Related Polypeptides

Polypeptides such as those corresponding in amino acid residue sequence to a portion of the ST-FeSV v-fes oncoprotein were coupled to KLH, and were used to immunize 129 GIX+ mice as described before and in Niman et al., in *Monoclonal Antibodies and T Cell Products*, Katz ed., (Boca Raton, Florida, CRC Press, Inc., 1982), pp. 21-51. Spleen cells from those immunized mice were fused with SP2/0-Ag14 myeloma cells using polyethylene glycol (PEG) 1500 (J. T. Baker Chemco, Phillsburg, New Jersey); PEG solutions for fusion were prepared at least one month prior to use to promote fusion efficiency. SP2/0-Ag14 cells did not produce their own Ig molecules, thereby facilitating isotype analysis and subsequent purification, such cells also do not produce retroviruses. The fused cells were then resuspended in 400 milliliters of Dulbecco's high-glucose minimal essential mediun (Flow Laboratories, Inc. Inglewood, California) containing 10 percent fetal calf serum, $1.0 \times 10^{-6}$ molar hypoxanthine, $1 \times 10^{-6}$ molar methotrextate, and $1.6 \times 10^{-5}$ molar thymidine. Next, the cells were plated into 30 microliter plates and grown as described in Niman et al., *Proc. Natl. Acad. Sci. U.S.A.*, 1982 supra.

2. sis- and myb-Related Polypeptides

Polypeptides (c) and (d) whose amino acid residues correspond to positions 139-155 of the predicted sequence of simian sarcoma virus transforming protein p28$^{sis}$ and to residues 2-18 of the predicted sequence of the avian myeloblastosis virus oncoprotein were synthesized and coupled to a KLH carrier as described above. The conjugates so prepared were administered at approximately 50 micrograms of polypeptide per 129 GIX+ mouse per injection.

On day 0 (zero), each conjugate was mixed with complete Freund's adjuvant and injected intraperitoneally. On day 19, each conjugate was admixed with alum to provide a concentration of 5 milligrams per milliliter of alum, and injected intraperitioneally. A booster injection of polypeptide (c) in phosphate-buffered saline was administered intraveneously on day 62. Serum containing oligoclonal antibodies was taken by orbital puncture on day 67. After a second alum-containing immunization of polypeptide (d) on day 41, the booster of polypeptide (d) was similarly admnistered on day 143 to similarly provide oligoclonal antibodies on day 148. The serum so obtained was tested for the antigenicity of its receptors as discussed in FIG. 4.

E. Antibody Binding Assay

Hybridomas producing anti-polypeptide antibodies were detected with an enzyme-linked immunoabsorbent assay (ELISA) method as discussed in the description of FIG. 4, herein, and in Niman et al., *Monoclonal Antibodies and T Cell Products*, supra. Briefly, approximately 50 micromoles of polypeptide were dried onto microliter plates, fixed with methanol, and incubated with hybridoma tissue culture supernatant. After thorough washing, hydridoma antibody binding was detected using rabbit anti-mouse kappa chain antibody (Litton Bionetics Inc., Kensington, Maryland) followed by a glucose oxidase conjugated goat anti-rabbit antisera. Binding was visualized with 2,2'-azino-di[3-ethyl-benzothiazoline-sulfonate (6)] (ABTS) dye (Bohringer-Mannheim, Indianapolis, Indiana) in the presence of glucose and horseradish peroxidase as described in Niman et al., *Monoclonal Antibodies and T Cell Products*, supra. Isotype was determined by substituting various rabbit anti-mouse lambda or heavy chain sera for the anti-mouse kappa chain as described above.

F. Electrophoretic Transfer and Immunoloqical Detection of Proteins on Nitrocellulose Cell extracts were subjected to polyacrylamide electrophoresis, and the protein was transferred to nitrocellulose (Schleicher and Schuell, Inc., Keene, New Hampshire) as discussed in the description of FIG. 5, herein, and in Niman et al., *Virology*, 123, 187-205 (1982). Peroxidase-labeled rabbit anti-mouse IgG serum (Tagol, Inc., Burlingame, California) diluted 1/1000 was incubated with the transfers for 1 hour at 25 degrees C. followed by washing as described in Niman and Elder, in *Monoclonal Antibodies and T Cell Products*, above. The bound antibody was visualized by incubation in 10 millmolar Tris (2-amino-2-(hydroxymethyl)-1,3-propanediol), pH 7.4, 0.009 percent $H_2O_2$ 0.0025 percent 3,3'-dimethoxybenzidine dihydrochloride (Eastman-Kodak, Co., Rochester, New York).

G. Preparation of Purified PDGF

Sixteen units of outdated platelets were obtained from the San Diego Blood Bank, San Diego, California. The purified PDGF used herein was obtained following the first two steps of the procedures described in Antonides et al., *Proc. Natl. Acad. Sci. USA*, 76, 1809–1813 (1979).

Briefly, platelets were collected by centrifugation at 28,000x gravity (g) for 20 minutes at 4 degrees C. The obtained platelets were washed by resuspension in 400 milliliters of a mixture containing (a) 9 volumes of 17 millimolar Tris-HCl, at pH 7.4 including 0.15 molar NaCl and 1% glucose; and (b) 1 volume of a solution that includes per 100 milliliters: 0.8 grams citric acid monohydrate, 2.2 grams anhydrous dextrose and 2.6 grams of sodium citrate dihydrate, followed by further centrifugation at 28,000xg for 10 minutes at 4 degrees C. The thus washed platelets were then resuspended in 16 milliliters of an aqueous solution containing 0.008 molar NaCl and 0.01 molar phosphate ion at pH 7.4 (NaCl-phosphate ion solution), and boiled for 10 minutes to lyse the cells.

Phenylmethyl sulfonyl fluoride and Traysylol (Sigma Chemical Co., St. Louis, Missouri), protease inhybitors, were added to the lysed cells at concentrations of 1 millimolar and 3%, respectively. The lysed cell mixture was again centrifuged to provide a pellet and a supernatant.

The supernatant was mixed with 8 milliliters of CM Sephadex C-50 (Pharmacia Fine Chemicals, Piscataway, New Jersey) beads that were previously equilibrated in the NaCl-phosphate ion solution. The beads and liquid were poured into a chromatography column (15×1.5 centimeters) that was washed with 6 column volumes of the above NaCl-phosphate ion solution. The PDGF, first eluate, was obtained by eluting the column with two column volumes of 1 molar NaCl. Traysylol was added to the eluate to provide a final concentration of 3%, and the eluate was dialyzed against the above NaCl-phosphate ion solution.

The above-produced lysed cell pellet was extracted with a 1 molar NaCl solution for 24 hours at 4 degrees C., and centrifuged. The supernatant was dialyzed against the above NaCl-phosphate ion solution, admixed with the above Sephadex, and made into a column. The column was washed and eluted as above to provide a second eluate that was dialyzed as above. The pellet prepared in this procedure was treated the same way to provide a third eluate that was again dialyzed as discussed before.

The, three dialyzed eluates were pooled and concentrated to a few milliliters of volume using an Amicon ultrafiltration apparatus (Amicon, Lexington, Massachusetts) and a filter having a 10k dalton exclusion. The PDGF so purified was then treated as discussed for FIG. 5.

Purified PDGF extract from approximately 2.5 units of platelets were mixed with a minimal volume of solution containing 0.5 percent sodium dodecyl sulfate (SDS) and 5 percent of 2-mercaptoethanol. The resulting mixture was boiled for two minutes and then electrophoresed therethrough a 5-17 percent polyacrylamide gel. The protein was thereafter electrophoretically transferred to nitrocellulose. (Niman and Elder, supra.) that was thereafter cut into strips, following the Western blot procedure.

The nitrocellulose strips so prepared were then treated with a solution containing 3 percent bovine serum albumin (BSA), 0.1 percent polyoxyethylene-9-octyl phenyl ether (Triton X-100) in phosphate buffered saline to inhibit non-specific protein binding. Four milliliters of mouse anti-serum diluted 1:200 were then incubated with the nitrocellulose strips.

After washing three times with a solution of 0.1 percent Triton X-100 in PBS, the nitrocellulose strips were incubated either with $10^6$ counts per minute of $^{125}$I-labeled *Staphylococus aureus* protein, or a 1:1000 dilution of peroxidase-conjugated goat anti-mouse serum (Tago), and again washed with 0.1 percent Triton X-100 in PBS. The preoxidase conjugate was developed with a solution containing 0.0009 percent $H_2O_2$, 0.0025 percent 3,3[1] - dimethoxybenzidine dihydrochloride (Eastman-Kodak, Co.,) in a 10 millimolar Tris buffer having a pH value of 7.4. The $^{125}$I labeled strips were developed by exposure on XRP-1 film (Eastman-Kodak Co.) using Cronex Hi-Plus (E.I. DuPont de Nemours & Co.) intensifying screens at minus 70° C. for 48 hours.

H. Urine Assay

Urine from donors (patients) as noted in the discussion of FIGS. 9 and 10 was collected and concentrated to a 200X using an Amicon ultrafiltration apparatus. This fluid was employed as the body fluid sample in the assay for proteins encoded by or related to sis and fes, ias, or myb antisera.

The urine sample was prepared in the following manner. The urine was clarified at 6000 r.p.m. at 4° C. for 10 minutes. The supernatant was then concentrated using an Amicon filter having a 10,000 dalton exclusion. This concentrated urine was then dialyzed to separate protein fractions.

Concentrated urine was electrophoresed at 20 microliters per lane into a 5–17% polyacrylamide gel and then electrophoresed onto nitrocellulose. The nitrocellulose filter was then probed with a 1/200 dilution of, for example, mouse antiserum in a solution 3% bovine serum albumin, 0.1% triton and PBS. The nitrocellulose filter was then washed three times and incubated with $10^6$ cpm $^{125}$I labeled protein A.

Binding was visualized with intensifying screens at −70° Centigrade as described in FIG. 6, supra.

I. Oncoproteins and Transformed Cells

NRK and SSV-transformed NRK cells were provided by S. A. Aaronson and K.C. Robbins of the Center for Cancer Research, National Institutes of Health, Bathesda, MD. The cells were grown in Dulbecco's minimal essential medium supplemented with 10% fetal calf serum, 2 millimolar L-glutamine, 100 IU per milliliter of penicillin and 100 micrograms per milliliter of streptomycin.

Parallel cultures of NRK and SSV-transformed NRK cells were washed 3 times for 2 hour intervals, and were then incubated for 18 hours in medium without serum at 15 milliliters per T75 centimeter$^2$ flask. The medium so conditioned was then centrifuged, and was stored frozen at −70° C.

The conditioned medium was thawed, concentrated 500-fold using dialysis in 1 molar acetic acid and was thereafter lyophilized. After solubilization and reduction with 10% 2-mercaptoethanol, 50 microliters of concentrated, conditioned media were electrophoresed into a 5–17% sodium dodecyl sulfatepolyacrylamide gel. Secreted proteins were then electrophoretically transferred and bound to nitrocellulose. Nonspecific binding was blocked by preincubation of the cell extract wth a solution containing 3% bovine serum albumin and 0.1% polyoxyethylene octyl phenyl ether in phosphate-buffered saline at a pH value of 7.4.

Prior to carrying out the immunological assays, 20 microliters of mouse antisera induced by PDGF-2(1-17) or PDGF-2(73-89) (described before) were preincubated with 100 micrograms of an appropriate polypeptide for 1 hour at 37° C. The oligoclonal antibody-containing/polypeptide reaction mixture was then diluted 1:500 with the above preincubation solution. The diluted solution so prepared was then contacted at 4° C. with the nitrocellulose-bound conditioned media, and that contact was maintained (incubated) for a time period of 15 minutes, a time sufficient for the immunoreaction of the antibody (receptor) and protein bound on the nitrocellulose. The nitrocellulose was thereafter washed.

The washed nitrocellulose was then contacted with affinity-purified rabbit anti-mouse $IgG^1$ antibodies (Litton) diluted 1:500 at 25° C. The contact was maintained for a time period of 2 hours sufficient for the anti-mouse $IgG_1$ antibodies to immunoreact with antibodies from the antisera that had bound to the nitrocellulose-bound secreted proteins of the conditioned media. The nitrocellulose was then washed again.

Immunoreaction (binding) was visualized with $10^6$ counts per minute of $^{125}$I-labeled *Staphylococcus aureus* protein A as described in Niman, *Nature,* 307, 180-183 (1984).

The foregoing is intended as illustrative of the present invention but not limiting. Numerous variations and modifications may be effected without departing from the true spirit and scope of the novel concepts of the invention.

What is claimed is:

1. A monoclonal receptor molecule of the Ig class that binds both (a) to a protein ligand, and (b) to a polypeptide having an amino acid residue sequence containing about 7 to about 40 amino acid residues corresponding to an amino acid residue sequence of a portion of said protein, said receptor molecule having been raised to an immunogen containing said polypeptide.

2. The monoclonal receptor molecule of claim 1 that:
(a) binds to a polypeptide encoded by the fes gene and having an amino acid residue sequence, from left to right and in the direction from amino-terminus to carboxy-terminus, represented by a formula selected from the group consisting of

SDVWSFGILLWETFSLGASPYPNLSNQQTR,

SPYPNLSNQQTR,

IHRDLAARNCLVTEKN,

IGRGNFGEVFSG,

LMEQCWAYEPGQRPSF,

VPVKWRAPEALNYGR, and

SSGSDVWSFGILLWE; and
(b) binds to an oncoprotein produced by cells expressing the fes gene.

3. The monoclonal receptor molecule of claim 1 that:
(a) binds to a polypeptide encoded by the myb gene and having an amino acid residue sequence, from left to right and in the direction from amino-terminus to carboxy-terminus represented by a formula selected from the group consisting of RRKVEQEGYPQESSKAG; and RHYTDEDPEKEKRIKELEL; and
(b) binds to an oncoprotein produced by cells expressing the myb gene.

4. The monoclonal receptor molecule of claim 1 that:
(a) binds to a polypeptide encoded by the sis gene and having an amino acid residue sequence, from left to right and in the direction from amino-terminus to carboxy-terminus represented by a formula selected from the group consisting of RKIEIVRKKPIFKKATV, and RVTIRTVRVRRPPKGKHRKC; and
(b) binds to an oncoprotein produced by cells expressing the sis gene.

5. The monoclonal receptor molecule of claim 1 that:
(a) binds to a polypeptide encoded by the ras gene and having an amino acid residue sequence, from left to right and in the direction from amino-terminus to carboxy-terminus, represented by a formula selected from the group consisting of YREQIKRVKDSDDVPMVLVGNKC, and

KLVVVGAR(S,V,G)GVGK;

wherein the amino acid residues in parentheses are each an alternative to the immediately preceding amino acid residue in the formula; and
(b) binds to an oncoprotein produced by cells expressing the ras gene.

6. The monoclonal receptor molecule of claim 1 that:
(a) binds to a polypeptide encoded by the myc gene and having an amino acid residue sequence, from left to right and in the direction from amino-terminus to carboxy terminus, represented by a formula selected from the group consisting of

CDEENFYQQQQQSEL,

PAPSEDIWKKFEL,

LPTPPLSPSRRSGLC,

CDPDDETFIKNIIIQDC,

CSTSSLYLQDLSAAASEC,

CASQDSSAFSPSSDSLLSSTESSP, and

CTSPRSSDTEENVKRRT; and
(b) binds to an oncoprotein produced by cells expressing the myc gene.

7. The monoclonal receptor molecule of claim 1 that:
(a) binds to a polypeptide encoded by the erb B gene and having an amino acid residue sequence, from left to right and in the direction from amino-terminus to carboxy terminus, represented by a formula selected from the group consisting of

ENDTLVRKYADANAVCQ

LGSGAFGTIYKG and

IMVKCWMIDADSRPKF; and (b) binds to an oncoprotein produced by cells expressing the erb-B gene.

8. The monoclonal receptor molecule of claim 1 that:
(a) binds to a polypeptide encoded by the mos gene and having an amino acid residue sequence, from left to right and in the direction from amino-terminus to carboxy terminus, represented by a formula selected from the group consisting of

LPRELSPSVDSR,

RQASPPHIGGTY, and

TTREVPYSGEPQ; and (b) binds to an oncoprotein produced by cells expressing the mos gene.

9. The monoclonal receptor molecule of claim 1 that:
(a) binds to a polypeptide encoded by the sis gene and having an amino acid residue sequence, from left to right and in the direction from amino-terminus to carboxy terminus, represented by a formula selected from the group consisting of

SLGSLTIAEPAMIAECK,

RKIEIVRKPIFKKATV,

RVTIRTVRVRRPPKGKHRKC, and

SIEEAVPAECKTR; and (b) binds to a protein selected from the group consisting of PDGF-1, PDGF-2 and an oncoprotein produced by cells expressing the sis gene.

10. A method of producing monoclonal receptor molecules to a protein molecule ligand comprising the steps of
(a) providing an immunogenic polypeptide or a conjugate of said polypeptide bound to a carrier, said polypeptide containing about 7 to about 40 amino acid residues and having an amino acid residue sequence corresponding to a portion of the amino acid residue sequence of a protein molecule ligand, said polypeptide as a conjugate bound to a keyhole limpet hemocyanin when used to immunize a mouse being sufficiently immunogenic and antigenic so as to provide a 50 percent binding titer of the immunized mouse' serum to said polypeptide of at least about a 1:400 dilution after three immunizations in a one-month period, each of said immunizations containing at least 10 micrograms of polypeptide in the conjugate, and utilizing complete Freund's adjuvant for the first immunization and thereafter alum adjuvant;
(b) hyperimmunizing a mammal with said polypeptide or with a conjugate of said polypeptide bound to a carrier to provide a hyperimmune serum containing receptor molecules that exhibit a 50 percent binding titer to said polypeptide of at least about a 1:400 dilution, the receptor molecules of said serum also binding to said protein molecule ligand to a portion of which said immunogenic polypeptide corresponds in amino acid residue sequence;
(c) maintaining said hyperimmunized mammal for a period of time sufficient for said 50 percent binding titer to said polypeptide of said serum to decline to a dilution of less than about 1:400;
(d) thereafter administering a booster immunization to said mammal with said polypeptide;
(e) fusing antibody-producing cells of the boosted mammal with myeloma cells within a period of about seven days from the day of booster administration to prepare hybridoma cells;
(f) assaying the hybridoma cells so prepared for the production of receptor molecules that bind to said protein molecule ligand to a portion of which said polypeptide corresponds in amino acid residue sequence; and
(g) culturing hybridoma cells producing receptor molecules that bind to said protein ligand to prepare an additional quantity of said hybridoma cells and the monoclonal receptors secreted by those cells.

11. The method of claim 10 further including the steps of
(e-1) assaying the hybridoma cells prepared in step (e) for the production of receptor molecules that bind to said polypeptide;
(e-2) culturing hybridoma cells that produce receptor molecules that bind to said polypeptide to prepare an additional quantity of such cells;
wherein the prepared hybridoma cells assayed in step (f) are those hybridoma cells prepared by culturing step (e-2), and the hybridoma cells cultured in step (g) bind to said polypeptide as well as to said protein ligand.

12. The method of claim 10 wherein said immunogenic polypeptide has an amino acid residue sequence, from left to right and in the direction from amino-terminus to carboxy-terminus, represented by a formula selected from the group consisting of

SDVWSFGILLWETFSLGASPYPNLSNQQTR,

SPYPNLSNQQTR,

IHRDLAARNCLVTEKN,

IGRGNFGEVFSG,

LMEQCWAYEPGQRPSF,

VPVKWTAPEALNYGR,

SSGSDVWSFGILLWE,

RRKVEQEGYPQESSKAG,

RHYTDEDPEKEKRIKELEL,

RKIEIVRKKPIFKKATV,

RVTIRTVRVRRPPKGKHRKC,

YREQIKRVKDSDDVPMVLVGNKC,

KLVVVGAR(S,V,G)GVGK,

CDEEENFYQQQQQSEL,

PAPSEDIWKKFEL,

LPTPPLSPSRRSGLC,

CDPDDETFIKNIIIQDC,

CSTSSLYLQDLSAAASEC,

CASQDSSAFSPSSDSLLSSTESSP,

LPRELSPSVDSR,

RQASPPHIGGTY,

TTREVPYSGEPQ.

SLGSLTIAEPAMIAECK,

RKIEIVRKKPIFKKATV,

RVTIRTVRVRRPPKGKHRKC,

SIEEAVPAECKTR,

ENDTLVRKYADANAVCQ,

LGSGAFCTIYKG(C), and

IMVKCWMIDADSRPKF wherein the amino acid residues in parentheses are each an alternative to the immediately preceding amino acid residue in the formula.

13. The method of claim 10 wherein said immunogenic polypeptide has an amino acid residue sequence, from left to right and in the direction from amino-terminus to carboxy-terminus, represented by a formula selected from the group consisting of

DPIPEELYEMLSDHSIRSF,

YREQIKRVKDSEDVPMVLVGNKC,

YTLVREIRQHKLRKLNPPDESGPGC,

YTLVREIRQYRLKKISKEEKTGC,

GSSKSKPKDPSQRRRS,

LGQGCFGEVWMG,

LMCQCWRKDPEERPTF,

LGEHHCTPSPPVDHG, and

IMVKCWMIDADSRPKF.

14. A diagnostic system for assaying for the presence of a protein ligand, said system including at least one package containing monoclonal receptor molecules of claim 1; a predetermined amount of said receptor molecules when admixed with a a predetermined amount of an aqueous composition to be assayed for the presence of a protein ligand forming a complex between said receptor and said ligand, when the protein ligand includes an amino acid residue sequence corresponding to the amino acid residue sequence of the polypeptide bound by said receptor molecule.

15. The diagnostic system of claim 14 further including a second package including a reactive label for identifying the presence of said complex.

16. The diagnostic system of claim 14 wherein said polypeptide to which said receptor binds has an amino acid residue sequence, from left to right and in the direction from amino-terminus to carboxy-terminus, represented by a formula selected from the group consisting of

SDVWSFGILLWETFSLGASPYPNLSNQQTR,

SPYPNLSNQQTR,

VPVKWTAPEALNTGR,

IHRDLAARNCVTEKN,

SSGSDVWSFGILLWE,

IGRGNFGEVFSG,

LMEQCWAYEPGQRPSF,

RPKVEQEGYPQESSKAG,

RHYTDEDPEKEKRIKELEL,

RKIEIVRKKPIFKKATV,

RVTIRTVRVRRPPKGKHRKC,

YREQIKRVKDSDDVPMVLVGNKC,

KLVVVGAR (S,V,G) GVVK

CDEEENFYQQQQQSEL,

PAPSEDIWKKFEL,

LPTPPLSPSRRSGLC,

CDPDDETFIKNIIIQDC,

CSTSSLYLQDLSAAASEC,

CASQDSSAFSPSSDSLLSSTESSP,

LPRELSPSVDSR

RQASPPHIGGTY,

TTREVPYSGEPQ,

SLGSLTIAEPAMIAECK,

RKIEIVRKKPIFKKATV,

RVTIRTVRVRRPPKGKHRKC,

SIEEAVPAECKTR,

ENDTLVRKYADANAVCQ,

LGSGAFGTIYKG, and

IMVKCWMIDADSRPKF wherein the amino acid residues in parentheses are each an alternative to the immediately preceding amino acid residue in the formula.

17. An affinity sorbant comprising an inert, solid support having linked thereto a receptor molecule of claim 1, said affinity-sorbant forming a reversible receptor-ligand complex when admixed with an aqueous composition containing a protein ligand having an amino acid residue sequence corresponding to said amino acid residue sequence of said polypeptide bound by said receptor.

18. A method of obtaining proteins in purified form comprising the steps of
 (a) providing the affinity sorbant of claim 17;
 (b) providing an aqueous composition containing a protein having an amino acid residue sequence corresponding to the amino acid residue sequence of the polypeptide to which the linked receptor of said affinity sorbant binds;
 (c) admixing said affinity sorbant and said aqueous composition to form a reversible, linked receptor-ligand complex between said receptor and said protein of step (b);

(d) separating the linked receptor-ligand complex from said aqueous composition to thereby obtain said protein in purified form linked to said affinity sorbant;

(e) dissociating said receptor-ligand complex; and, (f) separating said purified protein from said affinity sorbant to provide said purified protein free from said affinity sorbant.

19. The monoclonal receptor of claim 1 secreted by the hybridoma designated ATCC HB 8596.

20. The monoclonal receptor of claim 1 secreted by the hybridoma designated ATCC HB 8595.

21. The monoclonal receptor of claim 1 secreted by the hybridoma designated ATCC HB 8594.

22. The monoclonal receptor of claim 1 secreted by the hybridoma designated ATCC HB 8593.

23. The hybridoma designated ATCC HB 8596 and secreting a monoclonal receptor of claim 1.

24. The hybridoma designated ATCC HB 8595 and secreting a monoclonal receptor of claim 1.

25. The hybridoma designated ATCC HB 8594 and secreting a monoclonal receptor of claim 1.

26. The hybridoma designated ATCC HB 8593 and secreting a monoclonal receptor of claim 1.

27. The hybridoma designated ATCC HB 8679 secreting a monoclonal receptor of claim 1.

28. The monoclonal receptor of claim 1 secreted by the hybridoma designated ATCC HB 8679.

29. A monoclonal receptor molecule of the Ig class that binds both (a) to a protein ligand encoded by or related to a retrovirus gene, and (b) to a polypeptide having an amino acid residue sequence containing about 7 to about 40 amino acid residues corresponding to an amino acid residue sequence of a portion of said protein encoded by or related to a gene of a retrovirus, said receptor molecule containing said polypeptide.

30. The monoclonal receptor molecule of claim 29 that (a) binds to a polypeptide encoded by the sis gene and having an amino acid residue sequence, from left to right and in the direction form the amino-terminus to carboxy terminus, represented by a formula selected from the group consisting of

SLGSLTIAEPAMIAECK,

RKIEIVRKKPIFKKATV,

RVTIRTVRVRRPPKGKHRKC, and

SIEEAVPAECKTR; and (b) binds to a protein selected from the group consisting of PGDG-1, PGDF-2 and an oncoprotein produced by cells expressing the sis gene.

31. A monoclonal antibody raised, by using an immunogenic polypeptide of about 7 to about 40 amino acids, said antibody being capable of binding to a protein containing the corresponding amino acid sequence of said polypeptide.

* * * * *

UNITED STATES PATENT AND TRADEMARK OFFICE
CERTIFICATE OF CORRECTION

PATENT NO. : 5,030,565　　　　　　　　　Page 1 of 3

DATED    : July 9, 1991

INVENTOR(S) : Henry L. Niman

It is certified that error appears in the above-indentified patent and that said Letters Patent is hereby corrected as shown below:

On drawing sheet, Fig. 9, the word "Sis" should be inserted in the left hand margin adjacent the band in he col. marked "A".

In column 1, line 12, insert the following:  This invention was made with government support under Public Health Service Contract N01-CP-41009, Public Health Service Grants CA 38160 and CA 25803 awarded by the National Institutes of Health.  The government has certain rights in the invention --.

| Column | Line | |
|---|---|---|
| 2 | 10 | The word "recombindant" should be spelled --recombinant--. |
| 6 | 15 | The word "immunication" should be spelled --immunization--. |
| 7 | 34 | The word "an" before "amino acid..." should be deleted. |
| 8 | 18 | The word "follwed" should be spelled --followed-- (our error). |
| 9 | 59 | The large circle in the center of the first parenthesis should be deleted. |
| 10 | 43 | The word "immunolgical" should be spelled --immunological--. |
| 10 | 67 | "$1.0^6$" should be --$10^6$--. |
| 11 | 15 | The word "Oligoclonae" should be spelled --Oligoclonal--. |
| 11 | 42 | The word "eft" should be --left--. |
| 14 | 23 | The word "the" at the end of the line should be deleted. |
| 18 | 34 | The word "inolculum" should be spelled --innoculum--. |
| 23 | 29 | The word "formulaes" should be spelled --formulae-- (our error). |

UNITED STATES PATENT AND TRADEMARK OFFICE
CERTIFICATE OF CORRECTION

PATENT NO. : 5,030,565                                   Page 2 of 3
DATED      : July 9, 1991
INVENTOR(S): Henry L. Niman It is certified that error appears in the above-indentified patent and that said Letters Patent is hereby corrected as shown below:

| Column | Line | |
|---|---|---|
| 35 | 14 | The word "follwed" should be spelled --followed--. |
| 40 | 14 | The word "preoxidase" should be spelled --peroxidase--. |
| 40 | 29 | The word "ias" should be spelled --ras--. |
| 43 | 26 | In claim 9, the group "RKIEIVRKPIFKKATV" should be changed to --RKIEIVRKKPIFKKATV--. |
| 45 | 31 | In claim 13, the group "YTLVREIRQYRLKKISKEEKTGC" should be changed to --YTLVREIRQYRLKKISKEEKTPGC--. |
| 45 | 65 | In claim 16, the group "VPVKWTAPEALNTGR" should be changed to --VPVKWTAPEALNYGR--. |
| 46 | 15 | In claim 16, the group "KLVVVGAR(S,V,G)GVVK should be changed to --KLVVVGAR(S,V,G)GVGK--. |

UNITED STATES PATENT AND TRADEMARK OFFICE
CERTIFICATE OF CORRECTION

PATENT NO. : 5,030,565
DATED : July 9, 1991
INVENTOR(S) : Henry L. Niman

It is certified that error appears in the above-indentified patent and that said Letters Patent is hereby corrected as shown below:

Column     Line

46     43     In claim 16, the group "LGSGAFGTIYKG" should be changed to --LGSGAFGTIYKG(C)--.

Signed and Sealed this

Twelfth Day of April, 1994

*Attest:*

BRUCE LEHMAN

*Commissioner of Patents and Trademarks*

*Attesting Officer*